(12) United States Patent
Duncan et al.

(10) Patent No.: US 11,459,362 B2
(45) Date of Patent: *Oct. 4, 2022

(54) RECOMBINANT POLYPEPTIES FOR MEMBRANE FUSION AND USES THEREOF

(71) Applicant: Entos Pharmaceuticals Inc., Edmonton (CA)

(72) Inventors: Roy Duncan, Mineville (CA); Eileen Kathryn Clancy, San Francisco, CA (US); John Lewis, London (CA); Roberto Justo De Antueno, Halifax (CA); Rae-Lynn Nesbitt, Port Stanley (CA)

(73) Assignee: ENTOS PHARMACEUTICALS INC., Edmonton (CA)

( * ) Notice: Subject to any disclaimer, the term of this patent is extended or adjusted under 35 U.S.C. 154(b) by 235 days.

This patent is subject to a terminal disclaimer.

(21) Appl. No.: 16/245,381

(22) Filed: Jan. 11, 2019

(65) Prior Publication Data
US 2019/0367566 A1 Dec. 5, 2019

Related U.S. Application Data

(63) Continuation of application No. 13/877,101, filed as application No. PCT/CA2011/001088 on Sep. 29, 2011, now Pat. No. 10,227,386.

(60) Provisional application No. 61/471,445, filed on Apr. 4, 2011, provisional application No. 61/438,155, filed on Jan. 31, 2011, provisional application No. 61/387,726, filed on Sep. 29, 2010.

(51) Int. Cl.
| C07K 14/46 | (2006.01) |
| A61K 9/127 | (2006.01) |
| C12N 15/113 | (2010.01) |
| C12N 15/11 | (2006.01) |

(52) U.S. Cl.
CPC ............ *C07K 14/46* (2013.01); *A61K 9/1271* (2013.01); *C12N 15/113* (2013.01); *C07K 2319/00* (2013.01); *C07K 2319/03* (2013.01); *C07K 2319/033* (2013.01); *C07K 2319/33* (2013.01); *C12N 15/111* (2013.01); *C12N 2310/14* (2013.01); *C12N 2320/32* (2013.01)

(58) Field of Classification Search
CPC .............. C07K 14/46; C07K 2319/00; C07K 2319/03; A61K 9/1271; C12N 15/113
USPC ........................................................ 424/450
See application file for complete search history.

(56) References Cited

U.S. PATENT DOCUMENTS

| 10,227,386 | B2* | 3/2019 | Duncan ................ C12N 15/113 |
| 2002/0045734 | A1 | 4/2002 | Duncan |
| 2009/0023215 | A1 | 1/2009 | Jessee et al. |

FOREIGN PATENT DOCUMENTS

| EP | 1339747 | 6/2005 |

OTHER PUBLICATIONS

Accardo, A. et al., "Peptide Modified Nanocarriers for Selective Targeting of Bombesin Receptors," Molecular BioSystems, © 2010 The Royal Society of Chemistry, Feb. 9, 2010, vol. 6, pp. 878-887.
Ciechonska, M, and Duncan, R, "Reovirus FAST proteins: virus-encoded cellular fusogens," Trends Microbiol., 22(12):715-724 (Dec. 2014).
Clancy, E. K., "Role of the Hydrophobic Regions of the Orthoreovirus FAST (Fusion-Associated Small Transmembrane) Proteins in Cell-Cell Mebrane Fusion" (Doctoral Thesis). Halifax, Nova Scotia: Dalhousie University, © 2009 Eileen K. Clancy, pp. 1-29.
International Search Report and Written Opinion of the International Searching Authority dated Jan. 26, 2012, issued in International Application No. PCT/CA2011/001088, 11 pages.
Lu, Y. et al., "Issues Related to Targeted Delivery of Proteins and Peptides," The AAPS Journal 2006 vol. 8, No. 3, pp. E466-E478.
Top, D. et al., "Liposome Reconstitution of a Minimal Protein-Mediated Membrane Fusion Machine," The EMBO Journal, © 2005 European Molecular Biology Organization, vol. 24, No. 17, pp. 2980-2988.

* cited by examiner

*Primary Examiner* — Yan Xiao
(74) *Attorney, Agent, or Firm* — Marshall, Gerstein & Borun LLP

(57) ABSTRACT

Disclosed is a recombinant polypeptide for facilitating membrane fusion. The recombinant polypeptide having a sequence with at least 80% sequence identity with the ectodomain of p14 fusion-associated small transmembrane (FAST) protein and having a functional myristoylation motif, a transmembrane domain from a FAST protein and a sequence with at least 80% sequence identity with the endodomain of p15 FAST protein. A targeting ligand can be added to the recombinant polypeptide for selective fusion. The recombinant polypeptide can be included in the membrane of a liposome, or the like, to facilitate the delivery of bioactive compounds, such as siRNA, or the recombinant polypeptide can be mixed with a lipid carrier and added to cultured cells to induce cell-cell fusion and heterokaryon formation.

**8 Claims, 24 Drawing Sheets
(14 of 24 Drawing Sheet(s) Filed in Color)
Specification includes a Sequence Listing.**

MGSGPSNFVNHAPGEAIVTGLEKGADKVAGTISHTIFVEIVSSSTGIIIAVGIFAFIFSFL
YKLLQWYNRKSKNKKRKEQIREQIELGLLSYGAGVASLPLLNVIAHNPGSVISATPIY
KGPCTGVPNSRLLQITSGTAEENTRILNHDGRNPDGSINV

FIG. 1A

MGSGPSNFVNHAPGEAIVTGLEKGADKVAGTISHTI{WE}

FIG. 1B

P15 (44) KLLQWYNRKSKNKKRKEQIREQIELGLLSYGAGVASLPLLNVIAHMPGS
P15       VISATPIYKGPCTGVPNSRLLQITSGTAEENTRILNHDGRNPDGSINV

FIG. 1C

ATGGGNWSNGGNCCNWSNAAYTTYGTNAAYCAYGCNCCNGGNGARGCNATHGT
NACNGGNYTNGARAARGGNGCNGAYAARGTNGCNGGNACNATHWSNCAYACNA
THTTYGTNGARATHGTNWSNWSNWSNACNGGNATHATHATHGCNGTNGGNATH
TTYGCNTTYATHTTYWSNTTYYTNTAYAARYTNYTNCARTGGTAYAAYMGNAAR
WSNAARAAYAARAARMGNAARGARCARATHMGNGARCARATHGARYTNGGNY
TNYTNWSNTAYGGNGCNGGNGTNGCNWSNYTNCCNYTNYTNAAYGTNATHGCN
CAYAAYCCNGGNWSNGTNATHWSNGCNACNCCNATHTAYAARGGNCCNTGYAC
NGGNGTNCCNAAYWSNMGNYTNYTNCARATHACNWSNGGNACNGCNGARGAR
AAYACNMGNATHYTNAAYCAYGAYGGNMGNAAYCCNGAYGGNWSNATHAAYG
TN

FIG. 1D

ATGGGGAGTGGACCCTCTAATTTCGTCAATCACGCACCTGGAGAAGCAATTGTA
ACCGGTTTGGAGAAGGGGCAGATAAAGTAGCTGGAACGATATCACATACGATT
TGGGAA

FIG. 1E

AAGTTGCTGCAGTGGTACAATCGTAAGTCAAAGAATAAGAAACGTAAAGAGCAA
ATTAGAGAACAAATTGAGCTTGGTTTATTATCATATGGTGCTGGAGTAGCATCAC
TTCCTTTGCTCAACGTTATTGCACATAATCCTGGATCAGTTATCTCGGCTACCCCT
ATCTATAAGGTCCGTGCACTGGTGTACCTAATTCGCGCCTACTTCAAATCACGA
GCGGGACTGCAGAAGAGAACACTAGAATTTTGAATCATGATGGAAGAAACCCAG
ATGGAAGTATCAACGTTTGA

FIG. 1F

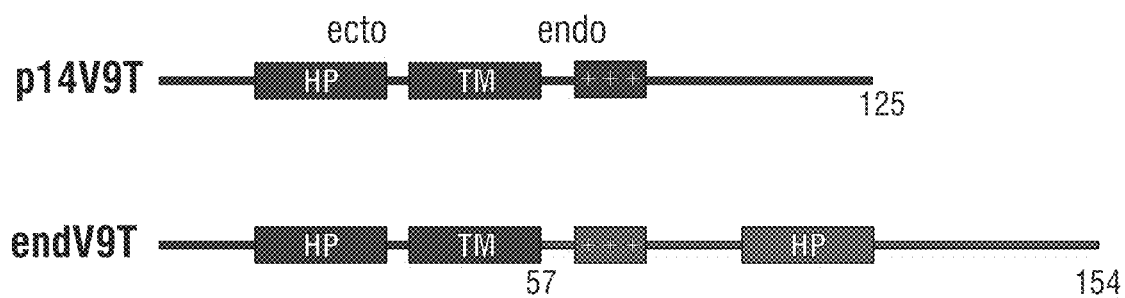
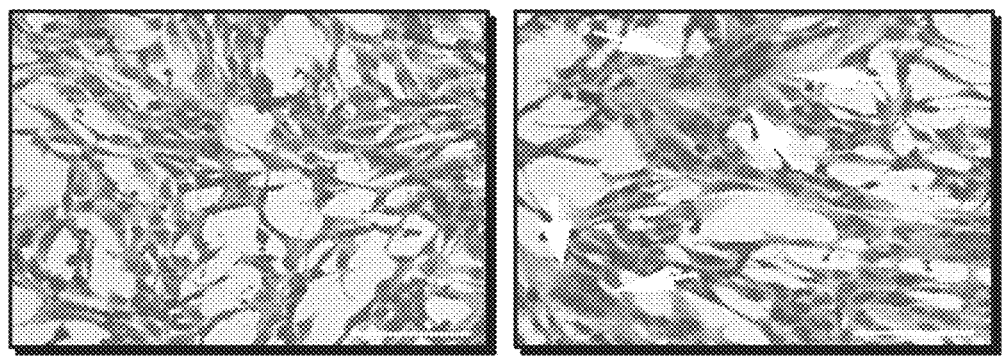
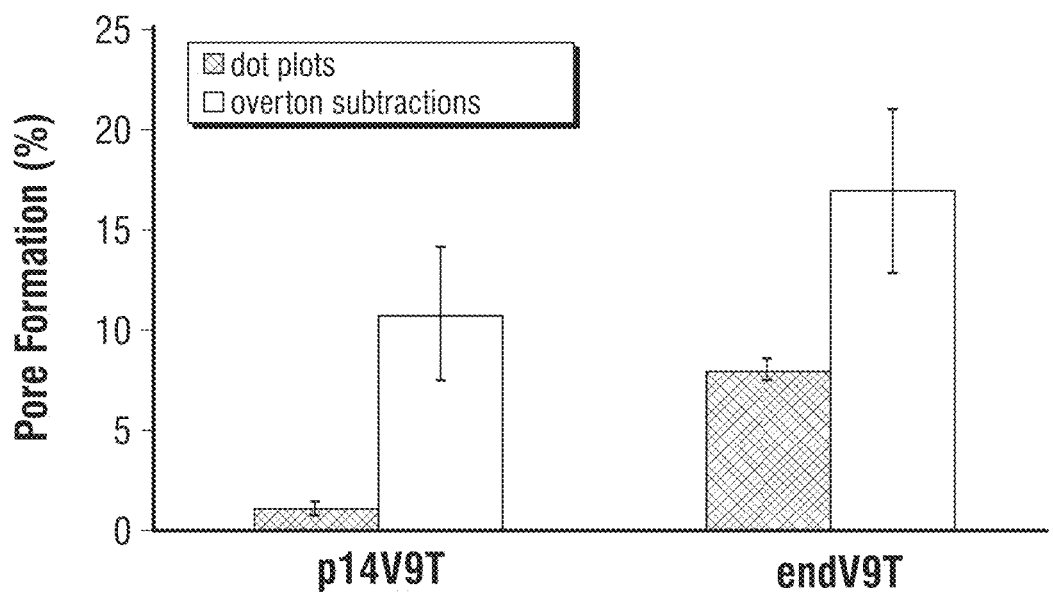
FIG. 6A
FIG. 6B
FIG. 6C p15HP     Ac-LGLLSYGAGVASLPLLNVIA-NH$_2$
p15HPscr    Ac-VLAPGLNALSLGVLASLIYG-NH$_2$
p14myr+    myr-GSGPSNFVNHAPGEAIVTGLEKGADKVAGT-NH$_2$
p14myr-     Ac-GSGPSNFVNHAPGEAIVTGLEKGADKVAGT-NH$_2$
*FIG. 10A*
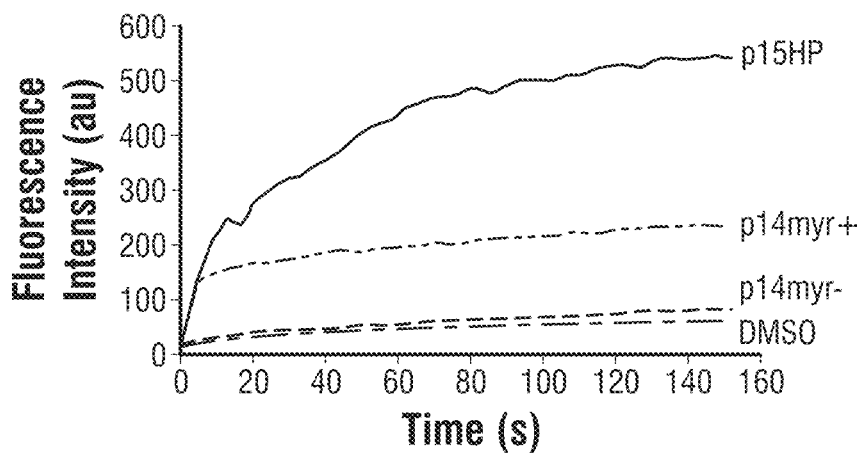
*FIG. 10B*
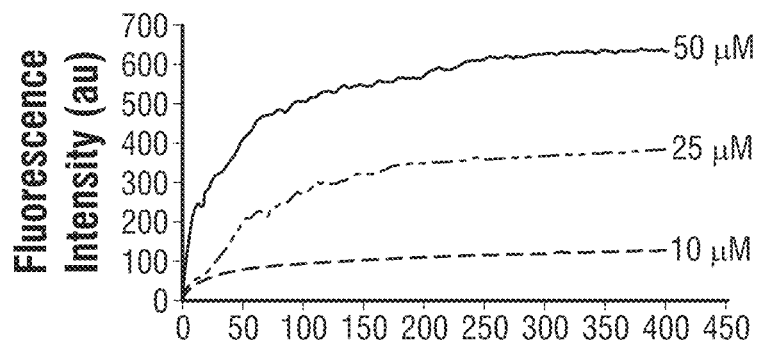
*FIG. 10C*
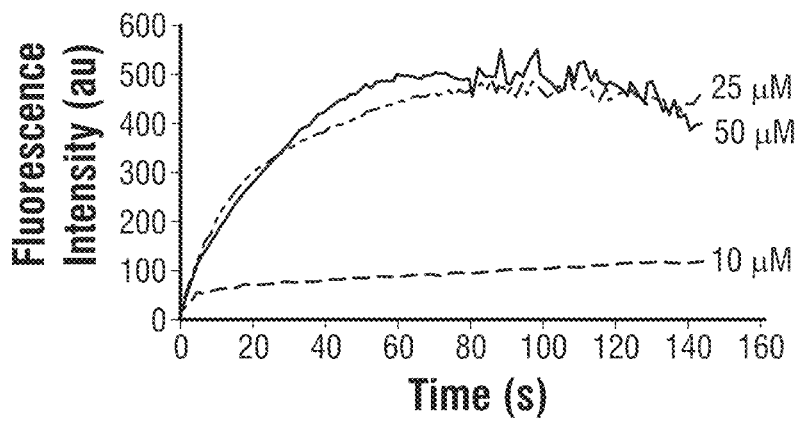
*FIG. 10D*

```
p15       IVSSSTGIIAVGIFAFIFSFLY
Δ21        VSSSTGIIAVGIFAFIFSFLY
Δ21/22      SSTGIIAVGIFAFIFSFLY
Δ40-43    IVSSSTGIIAVGIFAFIF
I21A      AVSSSTGIIAVGIFAFIFSFLY
IV21/22A  AASSSTGIIAVGIFAFIFSFLY
```
FIG. 11A
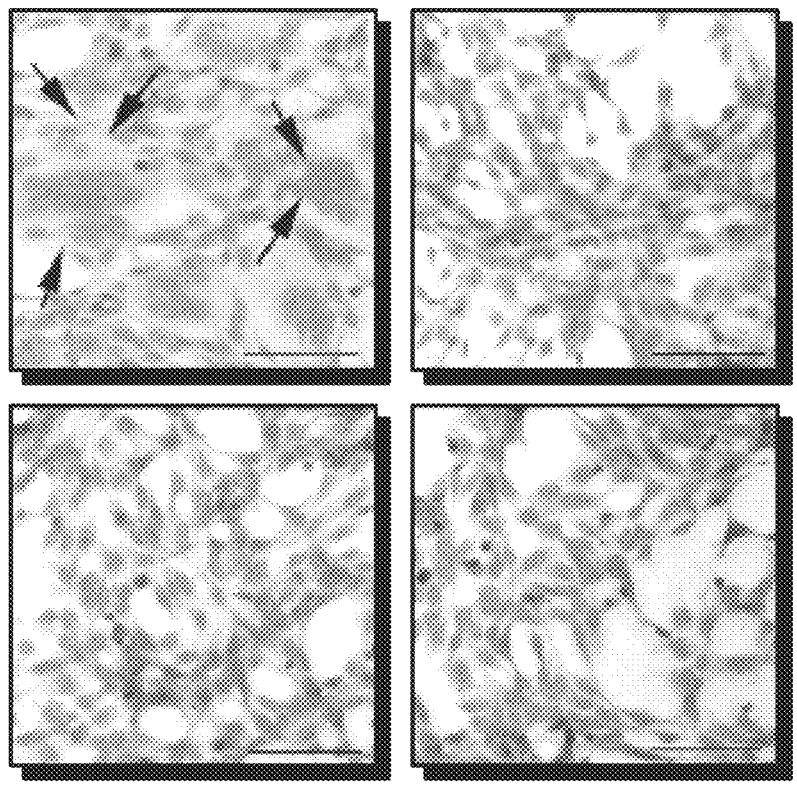
FIG. 11B
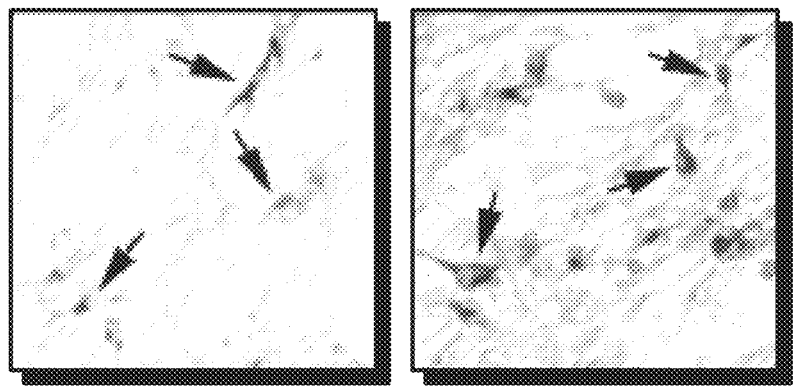
FIG. 11C

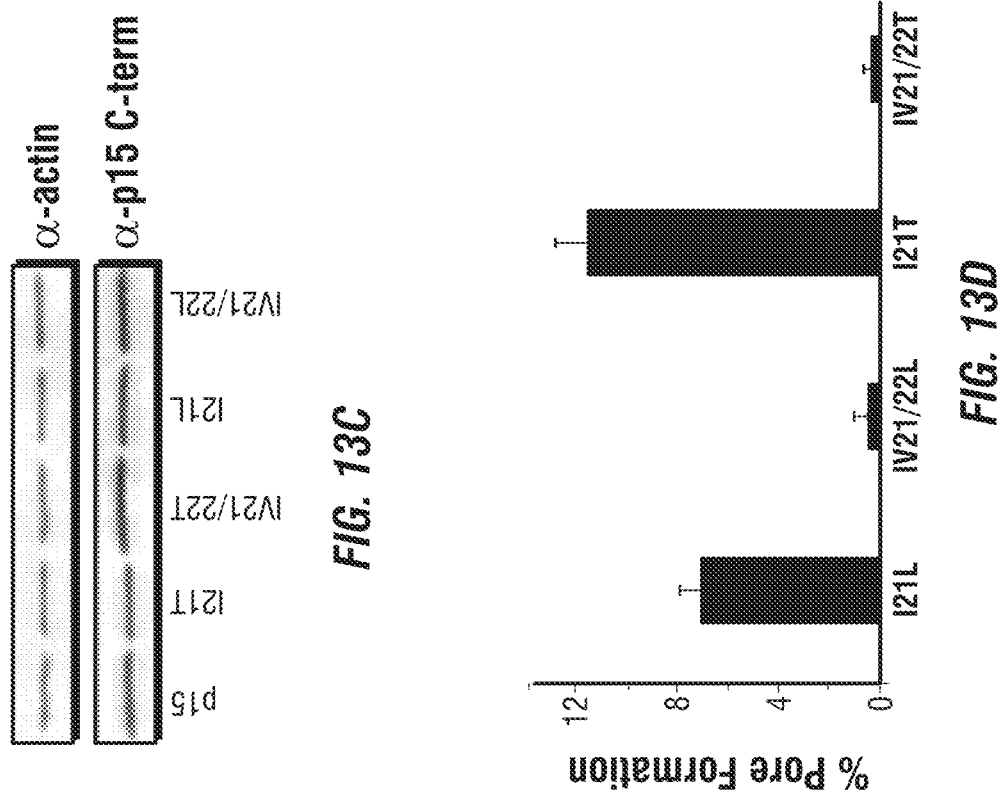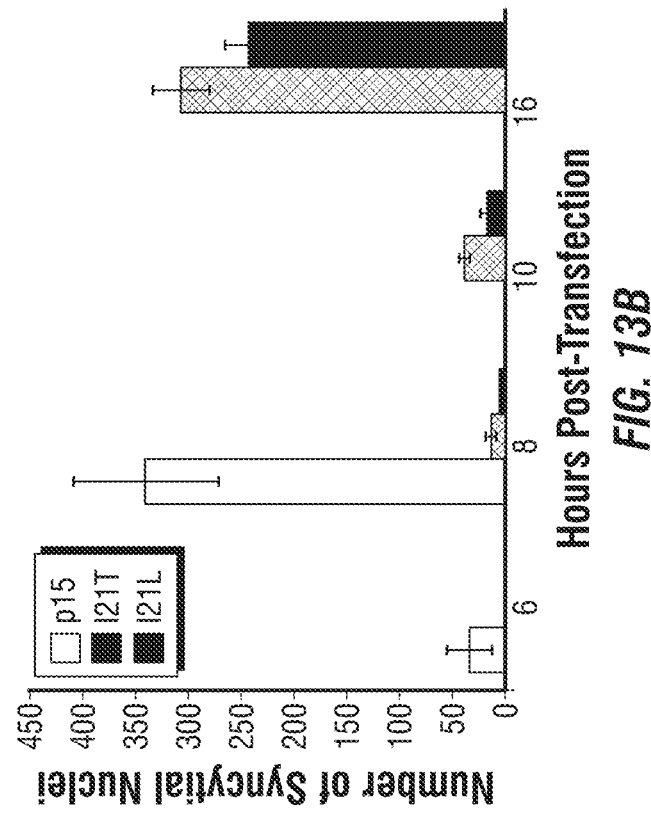
FIG. 13A
FIG. 13B
FIG. 13C
FIG. 13D

```
atggggagtggacccctctaattcgtcaatcacgcaccctggagaa
 M  G  S  G  P  S  N  F  V  N  H  A  P  G  E
gcaattgtaaccggtttggagaaagggcagataaagtagctggaacgatatcacatacg
 A  I  V  T  G  L  E  K  G  A  D  K  V  A  G  T  I  S  H  T
atttggaagtgatcgccggattagtagcccttgctgcattcttagcgtttggcttctgg
 I  W  E  V  I  A  G  L  V  A  L  L  T  F  L  A  F  G  F  W
ttgttcaagtatctccaaaagagaagaagacaactcactgattcccaaaaa
 L  F  K  Y  L  Q  K  R  E  R  R  Q  L  T  E  F  Q  K
cggtatctacggaatagctacaggttgagtgagatccagagacctatcacagcacgaa
 R  Y  L  R  N  S  Y  R  L  S  E  I  Q  R  P  I  S  Q  H  E
tacgaagacccatacgagcccaccagtcgcaccaagtcccccctccttatagcaca
 Y  E  D  P  Y  E  P  P  S  R  R  K  P  P  P  P  Y  S  T
tacgtcaacatcgataatgtctcagccattgatgacgacgaagcaccaccaccaccat
 Y  V  N  I  D  N  V  S  A  I  D  D  D  D  K  H  H  H  H
cac-gagcagaggctggggaatcagtgggtcagtgggtcacttgatgtaa
 H  E  Q  R  L  G  N  Q  W  A  V  G  H  L  M
```

FIG. 16

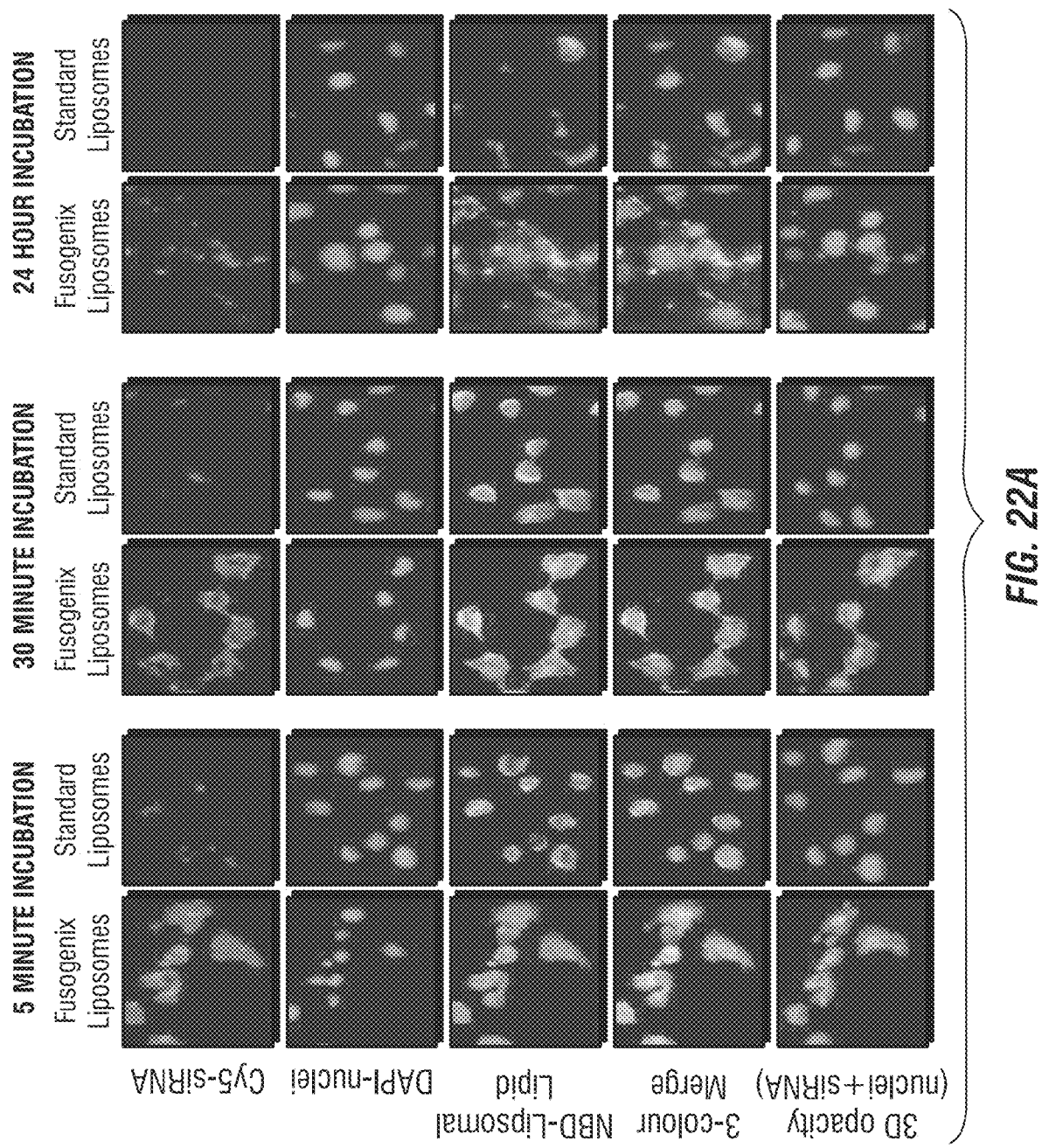

RECOMBINANT POLYPEPTIES FOR MEMBRANE FUSION AND USES THEREOF

CROSS-REFERENCE TO RELATED APPLICATIONS

The present application is a continuation of U.S. patent application Ser. No. 13/877,101, filed Jun. 5, 2014 (issued Mar. 12, 2019 as U.S. Pat. No. 10,227,386, which was a U.S. national-stage of PCT International Patent Application No. PCT/CA2011/001088 (nationalized), filed Sep. 29, 2011, which claims the benefit of U.S. Provisional Patent Application No. 61/471,445, filed Apr. 4, 2011, U.S. Provisional Patent Application No. 61/438,155, filed Jan. 31, 2011, and U.S. Provisional Patent Application No. 61/387,726, filed Sep. 29, 2010; the contents of each of which is specifically incorporated herein in its entirety by express reference thereto.

FIELD OF THE INVENTION

The invention generally relates to a recombinant protein for membrane fusion. More specifically, the invention relates to recombinant protein having sequences related to fusion-associated small transmembrane proteins.

BACKGROUND OF THE INVENTION

Membrane fusion reactions are common in eukaryotic cells. Membranes are fused intracellularly in processes including endocytosis, organelle formation, inter-organelle traffic, and constitutive and regulated exocytosis. Intercellularly, membrane fusion occurs during sperm-egg fusion and myoblast fusion.

Membrane fusion has been induced artificially by the use of liposomes, in which the cell membrane is fused with the liposomal membrane, and by various chemicals or lipids, which induce cell-cell fusion to produce heterokaryons. Naturally occurring proteins shown to induce fusion of biological membranes are mainly fusion proteins of enveloped viruses.

In liposome-based delivery systems, liposomes are used to encapsulate bioactive molecules inside lipid vesicles for delivery into the cell. There has been interest in using such delivery systems in treating various cancer, since, in theory, the use of liposomes will allow for a more targeted approach to treating the cancer cells [Arias et al., *Curr. Drug Targets*, March 28 (2011)]. However, the polar lipid head groups oriented on both surfaces of the lipid bilayer, along with an associated water layer, make spontaneous membrane fusion thermodynamically unfavorable. Moreover, the generalized release of the encapsulated bioactive molecules to both the cancerous cells and the healthy cells in a cancer inflicted tissue makes traditional liposome-based delivery systems less than perfect.

Various chemicals or lipids have been used to promote membrane fusion. However, these reagents usually exhibit cytotoxic effects [see, for example, Iwanoto et al., in *Biol. Pharm. Bull.* 19:860-863 (1996) and Mizugucji et al., in *Biochem. Biophys. Res. Commun.*, 218:402-407 (1996)].

It is generally believed that membrane fusion under physiological conditions is protein-mediated. This has lead to the development of liposomes that contain fusion-promoting proteins (proteoliposomes), with decreased cytotoxicity [see, for example, Cheng, *Hum. Gene Ther.* 7:275-282 (1996); Hara et al., *Gene*, 159:167-174 (1995); and Findeis et al., *Trends Biotechnol.*, 11:202-205 (1993)].

One particularly interesting group of proteins recently identified as fusion-promoting proteins are the fusion-associated small transmembrane (FAST) proteins. The FAST proteins are a unique family of membrane fusion proteins encoded by the fusogenic retroviruses (Duncan et al., *Virology*, 319:131-140 (2004). Currently, the FAST proteins include: p10, p14, p15 and p22. At 95 to 198 amino acids in size, the FAST proteins are the smallest known viral membrane fusion proteins. Rather than mediating virus-cell fusion, the FAST proteins are non-structural viral proteins that are expressed on the surfaces of virus-infected or -transfected cells, where they induce cell-cell fusion and the formation of multinucleated syncytia. A purified FAST protein, when reconstituted into liposome membranes, induces liposome-cell and liposome-liposome fusion, indicating the FAST proteins are bona fide membrane fusion proteins (Top et al., *EMBO J.* 24:2980-2988, 2005).

In contrast to most enveloped viral fusion proteins in which the cytoplasmic tail is extremely short relative to the overall size of the protein, the FAST proteins all have an unusual topology that partitions the majority of the protein to the membrane and cytoplasm, exposing ectodomains of just 20 to 43 residues to the extracellular milieu (Corcoran and Duncan, *J. Virol.*, 78(8):4342-51, 2004; Dawe et al., *J. Virol.*, 79(10):6216-26, 2005). Despite the diminutive size of their ectodomains, both p14 and p10 encode patches of hydrophobicity (HP) hypothesized to induce lipid mixing analogously to the fusion peptides encoded by enveloped viral fusion proteins (Corcoran et al., *J Biol Chem* 279(49): 51386-94, 2004; Shmulevitz et al., J Virol 78(6):2808-18, 2004). The p14 HP is comprised of the N-terminal 21 residues of the protein, but peptides corresponding to this sequence require the inclusion of the N-terminal myristate moiety to mediate lipid mixing. Nuclear magnetic resonance (NMR) spectroscopy revealed that two proline residues within the p14 HP form a protruding loop structure presenting valine and phenylalanine residues at the apex and connected to the rest of the protein by a flexible linker region (Corcoran et al., J Biol Chem 279(49): 51386-94, 2004). The p10 HP on the other hand, flanked by two cysteine residues that form an intramolecular disulfide bond, may have more in common with the internal fusion peptides of the Ebola virus and avian leukosis and sarcoma virus (ALSV) glycoproteins (Delos et al., *J Virol.*, 74(4):1686-93, 2000; Delos and White, *J. Virol.*, 74(20):9738-41, 2000; Gallaher, 1996; Ito et al., *J Virol.*, 73(10:8907-12, 1999; Ruiz-Arguello et al., *J. Virol.*, 72(3):1775-81, 1998), and likely adopts a cystine-noose structure that forces solvent exposure of conserved valine and phenylalanine residues for membrane interactions (Barry et al., *J. Biol. Chem.*, 285:16424, 2010). In contrast to p14 and p10, the 20 residue ectodomain of p15 completely lacks a hydrophobic sequence that could function as a traditional fusion peptide (Dawe et al., *J Virol* 79(10): 6216-26, 2005). In the absence of such a motif, the p15 ectodomain instead encodes a polyproline helix that has been proposed to function as a membrane destabilizing motif.

There is a need in the art for the targeted delivery of bioactive molecules encapsulated by liposomes.

SUMMARY OF THE INVENTION

It is an object of the present invention to provide a recombinant protein that can induce membrane fusion.

According to an aspect of the present invention there is provided a recombinant polypeptide for facilitating membrane fusion, said recombinant polypeptide comprising: an ectodomain comprising a sequence with at least 80% sequence identity with the sequence defined by SEQ ID NO:2 and comprising a functional myristoylation motif; a transmembrane domain comprising 23 amino acid residues, at least two hydrophobic, β-branched residues adjacent the ectodomain, three consecutive serine residues immediately adjacent the at least two hydrophobic, β-branched residues, and a glycine residue at positions 7 and 13 from the junction between the ectodomain and the first hydrophobic, β-branched residue; and an endodomain comprising a sequence with at least 80% sequence identity with the sequence defined by SEQ ID NO:3 or SEQ ID NO:4.

In one embodiment, the at least two hydrophobic, β-branched residues are selected from the group consisting of isoleucine and valine.

In another embodiment, the transmembrane domain is defined by a sequence having at least 80% sequence identity with the sequence defined by SEQ ID NO:11.

In a further embodiment, the ectodomain is defined by the sequence defined by SEQ ID NO:2.

In a yet further embodiment, the endodomain is defined by the sequence defined by SEQ ID NO:3 or SEQ ID NO:4.

According to another aspect of the present invention, there is provided a polypeptide defined by a sequence with at least 80% sequence identity with the sequence defined by SEQ ID NO:1.

In one embodiment, the polypeptide is defined by the sequence defined by SEQ ID NO:1.

According to an aspect of the present invention, there is provided a liposome comprising the recombinant polypeptide as described above.

According to a further aspect of the present invention, there is provided nucleic acid molecules encoding the recombinant polypeptides, and components thereof, described above.

According to a further aspect of the present invention, there is provided expression vectors comprising the nucleic acid molecules described above.

According to another aspect of the present invention, there is provided a polypeptide comprising 23 amino acid residues, at least two N-terminal hydrophobic, β-branched residues, three consecutive serine residues immediately adjacent the at least two hydrophobic, β-branched residues, and a glycine residue at positions 7 and 13 from the N-terminus of the polypeptide.

In one embodiment, the at least two hydrophobic, β-branched residues are selected from the group consisting of isoleucine and valine.

In another embodiment, the transmembrane domain is defined by a sequence having at least 80% sequence identity with the sequence defined by SEQ ID NO: 11.

According to another aspect of the present invention there is provided a liposome comprising a recombinant peptide embedded within the membrane of the liposome. The recombinant peptide comprises a fusion-associated small transmembrane protein linked to a targeting ligand.

In one embodiment, the fusion-associated small transmembrane protein is selected from the family Reoviridae.

In another embodiment, the fusion-associated small transmembrane protein is selected from the genus Orthoreovirus and Aquareovirus.

In a further embodiment, the genus Orthoreovirus comprises avian, mammalian and reptilian reoviruses.

In a yet further embodiment, the fusion-associated small transmembrane protein is selected from the group consisting of p10, p14, p15 and p22.

In a still further embodiment, the fusion-associated small transmembrane is a chimera of two or more domains of p10, p14, p15 and p22.

In a further embodiment, the fusion-associated small transmembrane protein is the recombinant polypeptide described above.

In another embodiment, the fusion-associated small transmembrane protein is defined by a sequence with at least 80% sequence identity with the sequence defined by SEQ ID NO: 1.

In an additional embodiment, the targeting ligand is bombesin.

Furthermore, the recombinant peptide is defined by the sequence depicted in SEQ ID NO:17.

According to another aspect of the invention, there is provided a recombinant polypeptide comprising a fusion-associated small transmembrane protein linked to a targeting ligand.

In one embodiment, the fusion-associated small transmembrane protein is selected from the family Reoviridae.

In another embodiment, the fusion-associated small transmembrane protein is selected from the genus Orthoreovirus and Aquareovirus.

In a further embodiment, the genus Orthoreovirus comprises avian, mammalian and reptilian reoviruses.

In a yet further embodiment, the fusion-associated small transmembrane protein is selected from the group consisting of p10, p14, p15 and p22.

In a still further embodiment, the fusion-associated small transmembrane is a chimera of two or more domains of p10, p14, p15 and p22.

In a further embodiment, the fusion-associated small transmembrane protein is the recombinant polypeptide described above.

In another embodiment, the fusion-associated small transmembrane protein is defined by a sequence with at least 80% sequence identity with the sequence defined by SEQ ID NO:1.

In an additional embodiment, the targeting ligand is bombesin.

Furthermore, the recombinant peptide is defined by the sequence depicted in SEQ ID NO:17.

According to a further aspect of the invention, there is provided a polynucleotide encoding the recombinant polypeptide as described above.

According to a yet further aspect of the invention, there is provided a host cell comprising the polynucleotide as described above.

According to an aspect of the present invention there is provided a method for delivering siRNA to a cell. The method comprising exposing a cell to a liposome comprising a membrane encircling an siRNA molecule and a fusogenic protein spanning the membrane of the liposome. The fusogenic protein being selected from p10, p14, 15, p22, the recombinant polypeptide described above, and combinations or variations thereof. Preferably, the fusogenic protein is the recombinant polypeptide described above, with or without the targeting ligand described above.

According to another aspect of the present invention there is provided a method for producing a liposome comprising a membrane encircling an siRNA molecule and a fusogenic protein spanning the membrane of the liposome. The method comprising the steps of: mixing siRNA with a liposome formulation to generate a core; encapsulating the core with a lipid to generate a liposome; saturating the liposome with a detergent; mixing a detergent-suspended fusogenic protein with the detergent saturated liposome in the presence of about 0.7-1.3% wt./vol. N-octyl β-D-glucopyranoside. The fusogenic protein being selected from p10, p14, p15, p22, the recombinant polypeptide described above, and combinations or variations thereof. The detergent is then removed from the fusogenic protein and liposome mixture; and the liposome comprising membrane encircling an siRNA molecule and a fusogenic protein spanning the membrane of the liposome isolated.

According to a further aspect of the present invention there is provided a liposome comprising an siRNA molecule encapsulated by a membrane embedded with a fusogenic protein. The fusogenic protein being selected from the group consisting of p10, p14, p15, p22, the recombinant polypeptide described above, and combinations and variations thereof. Preferably, the fusogenic protein is the recombinant polypeptide described above, with or without the targeting ligand described above.

According to a yet further aspect of the present invention there is provided use of the liposome described above for delivery of siRNA to a cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with regard to the following description and accompanying drawings wherein:

(FIG. 1A) is a representation of a linear amino acid sequence of a polypeptide of the present invention (SEQ ID NO:1); (FIG. 1B) is a representation of a linear amino acid sequence of a p14 ectodomain (SEQ ID NO:2); (FIG. 1C) is a linear amino acid sequence of the polypeptide sequence of a p15 endodomain (SEQ ID NO:3 and SEQ ID NO:4); (FIG. 1D) is a linear polynucleotide sequence encoding a polypeptide of the present invention (SEQ ID NO:5); (FIG. 1E) is a linear polynucleotide sequence encoding a p14 ectodomain (SEQ ID NO:6); and (FIG. 1F) is a linear polynucleotide sequence encoding a p15 endodomain (SEQ ID NO:7);

(FIG. 4B) percentage pore formation by dot plot or Overton subtraction from the experiment presented in panel (FIG. 4A). Results are presented as the means±standard deviation of a representative experiment done three times in triplicate; (FIG. 4C) the extent of pore formation induced by p14 and p14end15 was determined as above except that a titration was carried out and the indicated amounts of plasmid were transfected into QM5 cells. The x-axis values represent the amount of p14 or p14end15 plasmid transfected per 1 μg of total DNA;

(FIG. 5B) QM5 cells transfected with p14 or p14end15 and anti-p14ecto antiserum (1:20) was added 2 hours post-transfection. Arrows indicate the borders of syncytia; (FIG. 5C) surface expression determined by transfecting QM5 cells with p14, c78 or c78p15; (FIG. 5D) QM5 cells co-tranfected with the indicated amounts of plasmid expressing p14G2A or p14end15G2A and pcDNA3, to a total of 1 μg, then stained and analysed by flow cytometry. Results are expressed as means±standard deviation of a representative experiment done in triplicate;

FIG. 6A, FIG. 6B, and FIG. 6C are graphical representations showing (FIG. 6A) a linear representation of p14 or a p14end15 harbouring a V9T substitution. "TM" stands for transmembrane domain; "endo" stands for endodomain, "HP" stands for hydrophobic patch and "+++" stands for polybasic region; (FIG. 6B) Giesma stains of QM5 cells transfected with p14V9T (a) or endV9T (b) for 24 hours. Arrows indicate the borders of syncytia; (FIG. 6C) the extent of pore formation determined by co-transfection of GFP with pcDNA3, p14V9T, or endV9T at a 1:4 ratio. Results are shown as means±standard error of values obtained from dot plots (solid bars) adjusted to subtract background pcDNA3 pore formation or Overton subtractions (empty bars) from three experiments done in triplicate;

(FIG. 9B) Giesma stained cells transfected with p15P81A for 8 (a) or 24 (b) hours. Arrows indicate the borders of syncytia;

FIG. 10(A) is a schematic representation showing the linear amino acid sequences of synthetic peptides used to induce liposome-liposome fusion (SEQ ID NO:8, SEQ ID NO:9 and SEQ ID NO:10); (FIG. 10B) a graphical representation showing the ability of 50 μM of p15HP, p14myr+ or p14myr− synthetic peptides resuspended in DMSO, or the volume equivalent of DMSO, to mediate lipid mixing of 100 μM of lipid (1:1:1, DOPC:DOPE:Chol); (FIG. 10C) is a graphical representation showing the ability of 50, 25 or 10 μM of p15HPscr synthetic peptide resuspended in DMSO to induce lipid mixing; (FIG. 10D) is a graphical representation showing the ability of 50, 25 or 10 μM of p15HPscr synthetic peptide resuspended in DMSO to induce lipid mixing;

(FIG. 11A) is a linear representation of the transmembrane domains of the p15 of the present invention and deletion constructs (p15Δ21, p15Δ21/22 and p15Δ40-43) or N-terminal substitution constructs (p15I21A and p15I21/22A) (SEQ ID NO:11, SEQ ID NO:12, SEQ ID NO: 13, SEQ ID NO:14, SEQ ID NO: 15 and SEQ ID NO:16). (FIG. 11B) represents QM5 cells transfected with authentic p15 (a), p15Δ21 (b), p15Δ21/22 (c) or p15Δ40-43 (d) then methanol fixed and Giemsa-stained 10 hr post-transfection to detect syncytia formation (indicated by arrows in panel a). Scale bars=100 μm (FIG. 11C) represents QM5 cells transfected with p15I21A (a) or p15I21/22A (b) and immunostained 24 h post-transfection using polyclonal anti-p15. Arrows indicate antigen-positive single cell foci;

(FIG. 13(A) is a linear representation of the TMDs of authentic p15 and the β-branched substitution constructs (I21T, IV21/22T, I21L and IV21/22L) (SEQ ID NO:11). (FIG. 13B) is a graphical representation showing the average number of syncytial nuclei present in QM5 cells transfected with p15, p15I21L or p15I21T at 6 to 16 h post-transfection was quantified by microscopic examination of five random fields of Giemsa stained monolayers. The number of syncytial nuclei induced by authentic p15 exceeded countable levels after 8 h post-transfection. Results are the mean±S.D. from a representative experiment done in triplicate. (FIG. 13C) shows lysates from QM5 cells transfected with p15 or the indicated point mutant were analyzed by SDS-PAGE and immunoblotting using polyclonal anti-p15 C26 term, or anti-actin as a loading control. (FIG. 13D) QM5 cells transfected with the indicated β-branched substitution constructs were assessed for cell-cell pore formation at 9 h post-transfection using a dual color FACS-based fluorescent pore formation assay. Results are the mean±S.D. from a representative experiment done in triplicate indicating the percent of donor cells co-expressing EGFP and the indicated p15 construct that acquired the small, aqueous calcein red fluorescent cytoplasmic marker from target cells;

FIG. 16 represents a linear amino acid sequence and corresponding nucleic acid sequence of a recombinant polypeptide of the present invention (SEQ ID NO:17 and SEQ ID NO:18);

FIG. 22A and FIG. 22B are immunofluorescence images (FIG. 22A) and graphical representations (FIG. 22B) of Cy5-siRNA accumulation in HT1080 cells 5 mins, 30 mins and 24 hours after exposure to Cy5-siRNA containing liposomes having fusogenic proteins embedded in their membranes compared to delivery by standard liposomes.

DESCRIPTION OF THE INVENTION

Figure 2:
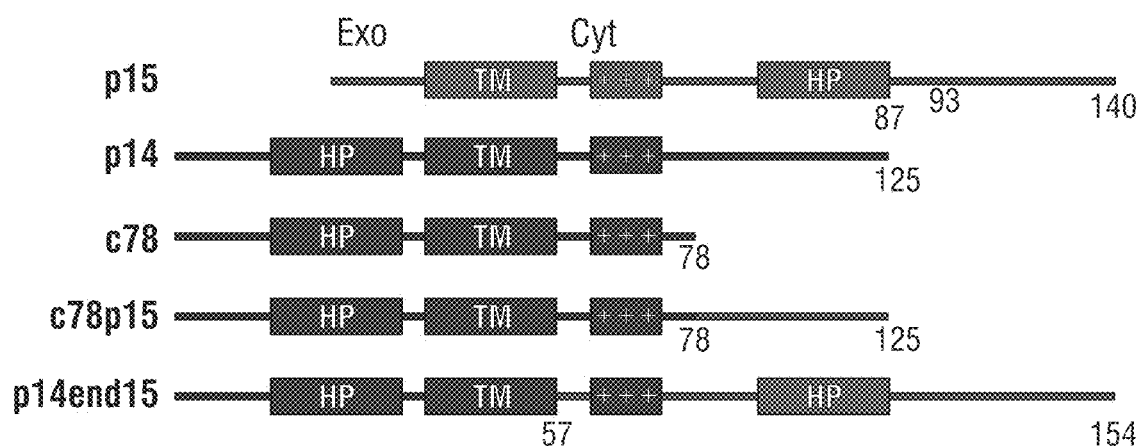
FIG. 2 is a schematic representation of wild type p15 and p14, p14 truncation (c78) and re-extension (c78p15) mutants, and p14end15, wherein "ecto" stands for ectodomain; "TM" stands for transmembrane domain; "endo" stands for endodomain, "HP" stands for hydrophobic patch and "+++" stands for polybasic region.
Figure 3:
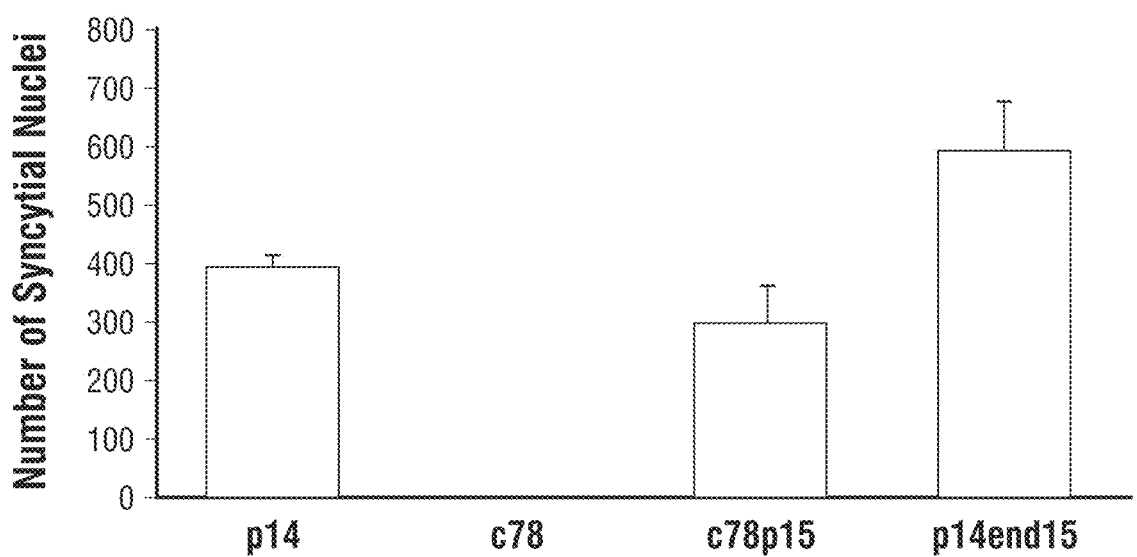
FIG. 3 is a graphical representation of QM5 cells transfected with p14, c78, c78p15 or p14end15, and the average number of syncytial nuclei per field as determined from Giemsa stained monolayers 8 hours post-transfection. Results are expressed as the means±standard deviation of a representative experiment done in triplicate.

The following description is of a preferred embodiment by way of example only and without limitation to the combination of features necessary for carrying the invention into effect.

The recombinant polypeptide of the present invention comprises a sequence corresponding to the ectodomain of p14 fusion-associated small transmembrane (FAST) protein, a transmembrane domain from a FAST protein and the endodomain of p15 FAST protein (FIG. 1A). In the case of FIG. 1A, the transmembrane domain comes from the p15 FAST protein. However, as described below, the transmembrane domain can come from any FAST protein, such as p14, p10 or p15. Preferably, the transmembrane domain comprises 23 amino acid residues, at least two hydrophobic, β-branched residues adjacent the ectodomain, three consecutive serine residues immediately adjacent the at least two hydrophobic, β-branched residues, and a glycine residue at positions 7 and 13 from the junction between the ectodomain and the first hydrophobic, β-branched residue. This polypeptide has been shown to increase syncytia formation compared to wild-type p14. This increase in syncytia formation also correlated with an increase in pore formation.

By "polypeptide" or "protein" is meant any chain of amino acids, regardless of length or post-translational modification (e.g., glycosylation or phosphorylation). Both terms are used interchangeably in the present application.

In one aspect of the invention, proteins are provided which are encoded by the genome of Reoviridae, and whose amino acid sequence is free of fusion peptide motifs.

The family Reoviridae includes the genus Orthoreovirus, which includes avian, mammalian and reptilian reoviruses, as well as the genus Aquareovirus.

The ectodomain or extracellular region of the p14 FAST protein is shown in FIG. 1B. As discussed below with respect to the transmembrane domains of the invention, the precise boundary of the p14 ectodomain is variable. As such, the last two residues of the p14 ectodomain [WE] could therefore be part of the transmembrane domain. The polynucleotide sequence of FIG. 1E includes codons corresponding to the WE amino acids. The composition of the p14 ectodomain has been described elsewhere (see Corcoran and Duncan, J Virol 78: 4342-4351, 2004; Corcoran et al., J Biol Chem 279:51386-51394, the contents of which are herein incorporated by reference). The p14 ectodomain contains a myristoylation motif, which is maintained in the recombinant polypeptide of the present invention.

In one embodiment, the myristoylation consensus sequence is: (initiator Met removed) Gly1-AA2-AA3-AA4-AA5-AA6-AA7-AA8-, where AA2, AA3, AA4, AA5, AA6 are small uncharged residues, AA3 and AA4 are preferably neutral, where AA5 is preferably serine or threonine, where AA6 is not proline, and where AA7 and AA8 are preferably basic (Towler et al., Annu. Rev. Biochem. 57:69-99 (1998); Resh, Biochim. Biophys. Acta. 1451:1-16 (1999), the contents of which are herein incorporated). In another embodiment, the myristoylation consensus sequence is G S G P S N F V (SEQ ID NO:19).

It is contemplated that sequence variation can occur between a functional p14 ectodomain and the wild-type sequence. For example, substitutions such as V9I, P 13A, G14A and E15A maintain fusion activity (Corcoran et al., J Biol Chem 279:51386-51394). As shown in FIG. 5A-FIG. 5D and FIG. 6A-FIG. 6C, when amino acids 1-21 of the p14 ectodomain are occupied by an anti-p 14ecto antibody, or when amino acid 9 of the p14 ectodomain is changed from valine to threonine, the recombinant polypeptide of the present invention is able to retain its ability to form syncytia. As such, variation in the wild-type p14 ectodomain sequence can occur while maintaining functionality of the recombinant polypeptide described herein.

As would be understood by a person skilled in the art, percent identity is measured using sequence analysis software such as the Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of identity is established by recording all of the positions in which the amino acids of both sequences are identical, relative to the total number of positions.

The proteins of the invention are structurally defined in that they are either encoded by Reoviridae are related to Reoviridae fusion proteins mainly at the transmembrane domain. Preferably the transmembrane domain comprises 23 amino acid residues, at least two hydrophobic, β-branched residues adjacent the ectodomain, three consecutive serine residues immediately adjacent the at least two hydrophobic, β-branched residues, and a glycine residue at positions 7 and 13 from the junction between the ectodomain and the first hydrophobic, β-branched residue.

The at least two hydrophobic, β-branched residues can be either isoleucine and valine. Preferably, the N-terminal hydrophobic, β-branched residue is isoleucine followed by valine.

Preferably, the transmembrane domain is represented by the sequence shown in FIG. 11A-FIG. 11C. However, other than the above-described considerations, variability from the sequence shown in FIG. 11A is contemplated.

The endodomain or cytoplasmic region of the p15 FAST protein is shown in FIG. 1C. The p15 endodomain comprises a hydrophobic patch, which is typically found on ectodomains, or extracellular regions, of many fusion proteins. Hydrophobicity values are determined according to methods known in the art. According to the present invention, the values are calculated using the normalized hydrophobicity scale of Eisenberg, Ann. Rev. Biochem., 53:595-623, 1984.

The p15 endodomain hydrophobic patch is a short sequence of about 20 residues containing an unusually high proportion of glycine and alanine. For example, 30% of the hydrophobic patch contains glycine or alanine. Within the hydrophobic patch, two glycine and one proline residues are required for syncytia and pore formation in the recombinant polypeptide. In addition to the hydrophobic patch, a polybasic region exists in a stretch of 40 residues that includes the hydrophobic patch.

One aspect of the invention provides sequences that are identical or substantially identical to the sequences of FIG. 1A-FIG. 1F. By "amino acid sequence substantially identical" is meant a sequence that is at least 80%, preferably 90%, more preferably 95% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan and cysteine.

Proteins having a sequence homologous to the sequences of FIG. 1A-FIG. 1F include naturally occurring allelic variants, as well as mutants or any other non-naturally occurring variants that retain the membrane fusion properties of the polypeptides of the sequences of FIG. 1A-FIG. 1F. As is known in the art, an allelic variant is an alternate form of a polypeptide that is characterized as having a substitution, deletion, or addition of one or more amino acids that retain the biological function of the polypeptide, i.e., the membrane-fusion activity.

Homologs and fragments thereof that do not occur naturally are designed using known methods for identifying regions of the protein that are likely to tolerate amino acid sequence changes and/or deletions. As an example, homologous polypeptides from different species are compared; conserved sequences are identified. The more divergent sequences are the most likely to tolerate sequence changes. Percent identity and similarity among sequences may be analyzed using, as an example, the BLAST homology searching algorithm of Altschul et al., *Nucleic Acids Res.* 25:3389-3402, 1997. Alternatively, a particular amino acid residue or sequence within the polypeptide can be mutated in vitro, then the mutant polypeptides screened for their ability to promote membrane fusion.

According to one aspect of the invention, isolated polynucleotides are provided which encode the membrane fusion proteins of the invention. In one embodiment, the polynucleotides are those shown in FIG. 1A-FIG. 1F. However, a person skilled in the art would readily understand and appreciate that redundancy in the genetic code allows for some variation in the actual polynucleotide sequences that encodes for the membrane fusion proteins of the invention. For example, the standard genetic code provides that the codons: CCT, CCC, CCA and CCG encode for proline.

The term "isolated polynucleotide" is defined as a polynucleotide removed from the environment in which it naturally occurs. For example, a naturally-occurring DNA molecule present in the genome of a living virus or as part of a gene bank is not isolated, but the same molecule separated from the remaining part of the viral genome, as a result of, e.g., a cloning event (amplification), is isolated. Typically, an isolated polynucleotide molecule is free from polynucleotide regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the proteins of the invention as shown in FIG. 1A-FIG. 1F is (a) a coding sequence, (b) a ribonucleotide sequence derived from transcription of (a), or (c) a coding sequence which uses the redundancy or degeneracy of the genetic code to encode the same polypeptides.

Homologous polynucleotide sequences are defined in a similar manner to homologous amino acid sequences. Preferably, a homologous polynucleotide sequence is one that is at least 45%, more preferably 60%, and most preferably 85% identical to sequence encoding the proteins of the invention, or to the coding sequences of the sequences shown in FIG. 1D-FIG. 1F, or to the sequence encoding the proteins shown in FIG. 1C.

Polynucleotides encoding homologous polypeptides or allelic variants are retrieved by polymerase chain reaction (PCR) amplification of genomic viral polynucleotides extracted by conventional methods. This involves the use of synthetic oligonucleotide primers matching upstream and downstream of the 5' and 3'ends of the coding region.

Suitable primers are designed according to the nucleotide sequence information provided in FIG. 1A-FIG. 1F. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 gel, 20 to 200 pM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for denaturation of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Current Protocols in Molecular Biology, John Wiley & Sons Inc., 1994), Silhavy et al., (Experiments with Gene Fusions, Cold Spring Harbor Laboratory Press, 1984), and Davis et al., (A Manual for Genetic Engineering: Advanced Bacterial Genetics, Cold Spring Harbor Laboratory Press, 1980). Important parameters for optimizing hybridization conditions are reflected in a formula used to obtain the critical melting temperature above which two complementary DNA strands separate from each other (Casey and Davidson, Nucl. Acids Res., 4:1539, 1977). For polynucleotides of about 600 nucleotides or larger, this formula is as follows: $T_m=81.5+0.41\times(\% \text{ G+C})+16.6 \log$ (cation ion concentration)$-0.63\times(\%$ formamide)$-600/$base number. Under appropriate stringency conditions, hybridization temperature ($T_h$) is approximately 20 to 40° C., 20 to 25° C., or, preferably 30 to 40° C. below the calculated $T_m$.

Those skilled in the art will understand that optimal temperature and salt conditions can be readily determined.

Polynucleotide molecules according to the invention, including RNA, DNA, or modifications or combinations thereof, have various applications. A DNA molecule is used, for example, (i) in a process for producing the encoded polypeptide in a recombinant host system, (ii) as part of a gene delivery system, e.g., liposomes, which, upon delivery, becomes expressed and promote membrane fusion, (iii) operably linked to regulatory elements as part of an expression cassette which, when turned on, expresses the polynucleotide and promote membrane fusion, and, (iv) as a probe or primer.

Accordingly, one aspect of the invention encompasses (i) an expression cassette containing a polynucleotide of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic host cell transformed or transfected with an expression cassette and/ or vector of the invention, under conditions that allow expression of the DNA molecule of the invention without being toxic to the host cell and, recovering the encoded polypeptide or polypeptide derivative from the host cell culture.

A recombinant expression system is selected from procaryotic and eucaryotic hosts. Since the proteins of the invention promote membrane fusion, host cells ale selected which can be maintained and which can express the proteins within tolerable limits of toxicity. Eucaryotic hosts include yeast cells (e.g., *Saccharomyces cerevisiae* or *Pichia pastoris*), plant cells, and cells which preferably have a cell wall so that the integrity of the host cell is not affected by the fusion activity. A preferred expression system is a procaryotic host such as *E. coli*. Bacterial and eucaryotic cells are available from a number of different sources including commercial sources to those skilled in the art, e.g., the American Type Culture Collection (ATCC; Manassas, Va., USA). Commercial sources of cells used for recombinant protein expression also provide instructions for usage of the cells.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen such that it is not affected by the fusion activity of the expressed membrane fusion protein. In addition, a host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variables are the relative strength of the sequence (e.g., the ability to drive expression under various conditions), the ability to control the sequence's function, compatibility between the polynucleotide to be expressed and the control sequence (e.g., secondary structures are considered to avoid hairpin structures which prevent efficient transcription). In selecting the host, unicellular hosts are selected which are: compatible with the selected vector, tolerant of any possible toxic effects of the expressed product, able to express the product efficiently, able to express the product in the desired conformation, easily scaled up, and easy to use for purifying the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide; a polynucleotide of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system.

Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* [as described in U.S. Pat. No. 5,028,530 and in Cagnon et al. (*Protein Eng.*, 4(7):843, 1991)]; the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., *J Bacterial.*, 169:5692, 1987).

Promoters contemplated for use herein include inducible (e.g., minimal CMV promoter, minimal TK promoter, modified MMLV LTR), constitutive (e.g., chicken alpha-actin promoter, MMLV LTR (non-modified), DHFR), and/or tissue specific promoters.

Inducible promoters contemplated for use in the practice of the present invention comprise transcription regulatory regions that function maximally to promote transcription of mRNA under inducing conditions. Examples of suitable inducible promoters include DNA sequences corresponding to: the *E. coli* lac operator responsive to IPTG (see Nakamura et al., *Cell*, 18:1109-1117, 1979); the metallothionein promoter metal-regulatory-elements responsive to heavy-metal (e.g., zinc) induction (see Evans et al., U.S. Pat. No. 4,870,009); the phage T7lac promoter responsive to IPTG (see Studier et al., *Methods Enzymol.*, 185:60-89, 1990; and U.S. Pat. No. 4,952,496), the heat-shock promoter; the TK minimal promoter; the CMV minimal promoter; a synthetic promoter; and the like.

The expression cassette is typically part of an expression vector, which is selected for its ability to replicate in the chosen expression system. Expression vectors (e.g., plasmids or viral vectors) can be chosen, for example, from those described in Pouwels et al., (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained through methods known in the art.

The recombinant polypeptide described above can also be linked to a targeting ligand. Alternatively, a fusion-associated small transmembrane (FAST) protein can be linked to a targeting ligand to facilitate binding of the liposome containing the FAST protein/targeting ligand to a specific cell type.

FAST proteins have been described elsewhere, see, for example, U.S. Pat. No. 7,851,595 to Duncan (the contents of which are specifically incorporated herein in its entirety by express reference thereto). Generally, the FAST proteins are membrane fusion proteins whose amino acid sequences are free of any fusion peptide motifs and which are related to Reoviridae in that they comprise an amino acid sequence which has at least 33% overall identity to the membrane fusion protein encoded by Reoviridae, and comprise a transmembrane domain whose amino acid sequence has at least 60% amino acid sequence identity to the transmembrane domain of the membrane fusion protein encoded by Reoviridae. In this case, fusion peptide motifs can be either be the type I or type II motifs. The fusion peptide motif (type I) is an amino acid sequence typically 17 to 28 residues long, with a hydrophobicity of about 0.6 to 0.7, and whose content of alanine plus glycine is about 29 to 43%. A fusion peptide motif (type II) is 16 to 20 residues long, has a hydrophobicity value about 0.3 to 0.4, has an alanine plus glycine content of about 29 to 43%; and contains a heptad repeat.

The FAST proteins are encoded by, or related to, the genome of Orthoreovirus or Aquareovirus, or the genome of a reovirus which naturally infects a poikilothermic host. Furthermore, the proteins of the invention are membrane fusion proteins whose amino acid sequences are free of any fusion motif, as defined above, and which are related to Orthoreovirus or Aquareovirus in that they comprise an amino acid sequence which has at least 33% overall identity to the membrane fusion protein encoded by Orthoreovirus or Aquareovirus, and comprise a transmembrane domain whose amino acid sequence has at least 60% amino acid sequence identity to the transmembrane domain of the membrane fusion protein encoded by Orthoreovirus or Aquareovirus.

As mentioned above, the recombinant polypeptide comprises a targeting ligand. For the purposes of the present invention, the targeting ligand refers to a polypeptide that is capable of recognizing and binding a cell surface molecule to facilitate the interaction between the cell and the liposome. For example, cells expressing gastrin-releasing peptide (GRP) receptors can be recognized by the targeting ligand, bombesin [Anastasi, A et al., *Experientia,* 27:166 (1971)]. GRP receptors have been shown to be expressed on the cell surface membranes of prostate cancer cells, but absent from normal prostate cells. This unique expression profile makes bombesin a preferred targeting ligand for the delivery of a substance encapsulated in liposome, such as a chemotherapeutic agent, to a cancerous prostate cell. Since normal, healthy prostate cells do not express GRP receptors, delivery of the chemotherapeutic agent to these cells will be limited.

Four GRP receptor sub-types have been identified to date: GRP-R, NMB-R, BRS-3 and BB4-R. A very potent universal pan-bombesin ligand with a structure of [D-Tyr6, β-Alai 1, Phe13, Nle14] bombesin-(6-14) has been shown to bind to all four GRP receptor subtypes with high affinity [Reubi, J C et al., *Clin. Cancer Res.,* 8:1139 (2002)].

A variety of targeted ligands have been described in the art. These include both peptides capable of being recognized by cell surface receptors, as well as antibodies that recognize and bind to cell surface receptors. Further examples of such targeting ligands include: protease-cleaved collagen IV (TLTYTWS); PC3 target (8-3) (DTDSHVNL); PC3 target (9-8)(DVVVALSDD); Linear RGDx1 (GRGDSG); and Linear RGDx3 (GRGDSGGRGDSGGRGDSG).

The use of liposomes having fusogenic proteins, as described herein, embedded in their membrane to deliver a payload, such as a bioactive compound, have been shown to be more effective in delivering the payload to a cell. For example, liposomes carrying an siRNA payload and having fusogenic proteins as described herein embedded in their membrane have been shown to more effectively reduce the expression of the targeted gene in a recipient cell compared to liposomes having no such fusogenic proteins in their membrane.

Various liposome compositions are known in the art. For example, neutral or anionic liposomes, and cationic lipids are known to facilitate delivery of substance(s) to a host cell. These compounds are readily available to one skilled in the art; for example, see Liposomes: A Practical Approach, RCP New Ed, IRL press (1990).

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides, such as siRNA.

Cationic lipids are also known in the art and are commonly used for drug or gene delivery. Such lipids include Lipofectin™ also known as DOTMA (N-[1-(2,3-dioleyloxy) propyls-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3-beta-(N—(N',N'-dimethyl aminomethane)-carbamoyl) cholesterol). A description of these cationic lipids can be found in EP Pat. No. 187,702, PCT Intl. Pat. Appl. Publ. No. WO 90/11092, U.S. Pat. No. 5,283,185, PCT Intl. Pat. Appl. Publ. No. WO 91/15501, PCT Intl. Pat. Appl. Publ. No. WO 95/26356, and U.S. Pat. No. 5,527,928. Cationic lipids for delivery of polynucleotides are preferably used in association with a neutral lipid such as DOPE (dioleyl phosphatidylethanolamine), as described in PCT Intl. Pat. Appl. Publ. No. WO 90/11092 as an example.

Formulations containing cationic liposomes may optionally contain other transfection-facilitating compounds.

A number of them are described in PCT Intl. Pat. Appl. Publ. Nos. WO 93/18759, WO 93/19768, WO 94/25608, and WO 95/02397. They include spermine derivatives useful for facilitating the transport of DNA through the nuclear membrane (see, for example, PCT Intl. Pat. Appl. Publ. No. WO 93/18759) and membrane-permeabilizing compounds such as GALA, Gramicidine S, and cationic bile salts (see, for example, PCT Intl. Pat. Appl. Publ: No. WO 93/19768).

Unilamellar liposomes of the present invention can be prepared from multilamellar lipid vesicles. For example, a mixture of DOPC:COPE:cholesterol:DC-cholesterol in a molar ratio of 60:30:4:6 can be used to prepare a multilamellar lipid vesicle suspension. However, lipid vesicles containing PE-PEG2000 and/or DOTAP may be required in certain circumstances. The multilamellar lipid vesicles can be prepared by a number of different methods, which will be known to a person skilled in the art, such as the thin film method described by Fenske and Cullis, 2005*, Methods Enzymol.,* 391:7-40.

Unilamellar liposomes can be extruded from the multilamellar lipid vesicle suspension by manual extrusion through a polycarbonate membrane of defined pore size, using gas-tight, glass syringes, such as the LiposoFast-Basic (Avestin, Inc., Ottawa, ON, CANADA). In this procedure, the sample is passed through the membrane by pushing the sample back and forth between two syringes. In most cases, a 50-nm diameter liposome will allow for a sufficient amount of siRNA to be packaged in the liposome to decrease expression of the target gene. In order to achieve a specific diameter of liposome, the multilamellar lipid vesicle suspension is passed through a filter having a specific diameter of pore size.

In one embodiment, the unilamellar liposomes are further processed to generate a wrapped liposome or wrapsome. Yagi et al., in *Cancer Res.* 2009, 69(16):6531-6538 describe a process for generating such wrapsomes. Briefly, a wrapsome core is generated using 100% DOTAP and reconstitution with a liposome buffer containing 4-(2-hydroxyethyl)-1-piperazineethanesulfonic acid, sodium chloride and phosphate buffered saline. The multilamellar wrapsome core is then further processed to isolate unilamellar wrapsomes with a diameter approximately equal to the diameter of the unilamellar liposomes described above. Prior to encapsulating the unilamellar liposomes described above with the wrapsome, siRNA is mixed with the unilamellar liposome to create an siRNA containing liposome. The wrapsomes are then dissolved in ethanol to create an envelope solution. This solution is then added to the siRNA containing liposome, in the presence of the liposome buffer described above, causing the envelope to wrap around the siRNA containing liposome to create a liposome capable of carrying a payload, such as siRNA to a cell.

The fusogenic proteins of the present invention can be inserted into the liposomal membrane by the detergent depletion method derived from the concepts outlined previously in such publications as Rigaud et al., 1995, *Biochim. Biophys. Acta*, 1231(3):223-46; Rigaud and Levy, 2003, *Methods Enzylmol.*, 372:65-86; and Top et al., 2005, *EMBO J.*, 24(17):2980-8, the contents of which are incorporated herein by reference. Briefly, the purified fusogenic protein is reconstituted into the liposomes by mixing the detergent-suspended fusogenic protein with liposomes pre-saturated with detergent, followed by removal of the detergent.

To assist in the process of inserting the fusogenic protein into the liposome membrane, n-octyl β-D-glucopyranoside (OG) is used in the detergent. Based on the size and type of liposomes used, an optimal concentration of OG should be determined by incrementally adding OG to a solution of liposomal lipids across a 0-2.0% final volume concentration spectrum. Absorbance is detected at $\lambda 600$ nm and a plot derived of absorbance versus OG %. The optimal concentration is just below the critical OG concentration which causes dissolution of the liposomes.

The liposomes of the present invention having fusogenic proteins embedded in their membranes are used to encapsulate small-interfering RNA or siRNA nucleic acids. siRNAs have been used to switch off genes in mammalian cells without initiating an acute phase response, i.e., a host defense mechanism that often results in cell death (Caplen et al., PNAS 98(17):9742-7, 2001; Elbashir et al., Methods 26(2):199-213, 2002). There is increasing evidence of post-transcriptional gene silencing by RNA interference (RNAi) for inhibiting targeted expression in mammalian cells at the mRNA level, in human cells. There is additional evidence of effective methods for inhibiting the proliferation and migration of tumor cells in human patients, and for inhibiting metastatic cancer development [see, e.g., Caplen et al. (supra)].

An siRNA is a nucleic acid that forms a double stranded RNA and has the ability to reduce or inhibit expression of a gene or target gene when the siRNA is delivered to or expressed in the same cell as the gene or target gene. siRNA is short double-stranded RNA formed by the complementary strands. Complementary portions of the siRNA that hybridize to form the double stranded molecule often have substantial or complete identity to the target molecule sequence. In one embodiment, an siRNA is a nucleic acid that has substantial or complete identity to a target gene and forms a double stranded siRNA.

When designing the siRNA molecules, the targeted region is selected from a given DNA sequence beginning 50 to 100 nucleotides downstream of the start codon. See, e.g., Elbashir et al., (supra). Initially, 5' or 3' UTRs and regions nearby the start codon were avoided assuming that UTR-binding proteins and/or translation initiation complexes may interfere with binding of the siRNP or RISC endonuclease complex. Sometimes regions of the target 23 nucleotides in length conforming to the sequence motif AA(N19)TT (N, an nucleotide), and regions with approximately 30% to 70% G/C-content (often about 50% G/C-content) often are selected. If no suitable sequences are found, the search often is extended using the motif NA (N21). The sequence of the sense siRNA sometimes corresponds to (N19) TT or N21 (position 3 to 23 of the 23-nt motif), respectively. In the latter case, the 3' end of the sense siRNA often is converted to TT. The rationale for this sequence conversion is to generate a symmetric duplex with respect to the sequence composition of the sense and antisense 3' overhangs. The antisense siRNA is synthesized as the complement to position 1 to 21 of the 23-nt motif. Because position 1 of the 23-nt motif is not recognized sequence-specifically by the antisense siRNA, the 3'-most nucleotide residue of the antisense siRNA can be chosen deliberately. However, the penultimate nucleotide of the antisense siRNA (complementary to position 2 of the 23-nt motif) often is complementary to the targeted sequence. For simplifying chemical synthesis, TT often is utilized. siRNAs corresponding to the target motif NAR (N17)YNN, where R is purine (A,G) and Y is pyrimidine (C,U), often are selected. Respective 21 nucleotide sense and antisense siRNAs often begin with a purine nucleotide and can also be expressed from pol III expression vectors without a change in targeting site. Expression of RNAs from pol III promoters can be more efficient when the first transcribed nucleotide is a purine.

The sequence of the siRNA can correspond to the full-length target gene, or a subsequence thereof. Often, the siRNA is about 15 to about 50 nucleotides in length (e.g., each complementary sequence of the double stranded siRNA is 15 to 50 nucleotides in length, and the double stranded siRNA is about 15 to 50 base pairs in length, sometimes about 20 to 30 nucleotides in length or about 20 to 25 nucleotides in length, e.g., 20, 21, 22, 23, 24, 25, 26, 27, 28, 29, or 30 nucleotides in length. The siRNA sometimes is about 21 nucleotides in length. Methods of using siRNA are known in the art, and specific siRNA molecules may be purchased from a number of companies including Dharmacon Research, Inc.

siRNA nucleic acids can be altered to form modified nucleic acid molecules. The nucleic acids can be altered at base moieties, sugar moieties or phosphate backbone moieties to improve stability, hybridization, or solubility of the molecule. For example, the deoxyribose phosphate backbone of nucleic acid molecules can be modified to generate peptide nucleic acids (see Hyrup et al., *Bioorg. Medicinal Chem.*, 4(1): 5-23 (1996)).

One aspect of the invention provides methods of using the proteins, polynucleotides and compositions of the invention. Accordingly, methods are provided to promote membrane fusion which comprise contacting the membranes to be fused with an effective amount of the above-described proteins.

Membranes contemplated for fusion in accordance with the present invention include cell membranes, liposome membranes, proteoliposome membranes, and the like.

In accordance with a still further embodiment of the present invention, there are provided methods for the production of liposome-liposome fusions or liposome-cell fusions, said methods comprising contacting lipids suitable for the formation of liposomes and a suitable cell in the presence of one or more proteins as described herein.

In accordance with yet another embodiment of the present invention, there are provided improved methods for the intracellular delivery of bioactive compounds employing liposomes, the improvement comprising incorporating into said liposomes one or more proteins as described herein.

The ability to promote efficient membrane fusion has broad applicability in clinical, industrial, and basic research situations. The recombinant proteins of the invention could be used as alternatives to chemically-induced membrane fusion to promote cell-cell fusion, for example, during the production of hybridoma cells for monoclonal antibody production. In this instance, the reovirus fusion proteins and the recombinant polypeptide thereof would be inducibly expressed from inside a transiently or permanently transfected cell population to trigger fusion of these cells with a target cell population.

The recombinant proteins also have application in enhancing liposome-cell fusion. Liposomes have been developed as a means to introduce nucleic acids, proteins, and metabolic regulators into cells. Although liposome-cell fusion has been amply demonstrated, the unfavourable thermodynamics of membrane fusion contribute to variable efficiencies of fusion and cytotoxicity which lead to the development of proteoliposomes-liposomes containing specific proteins to promote cell binding and fusion.

Most of the proteoliposome studies reported in the art relate to the use of various enveloped virus fusion proteins. In accordance with the present invention, it is possible to take advantage of the novel structural features associated with the recombinant proteins for use in proteoliposomes to enhance the intracellular delivery of bioactive compounds (e.g., nucleic acids, proteins or peptides, pharmacological agents, and the like), both in cell culture and in vivo.

The recombinant proteins described herein have the ability to promote membrane fusion in a diversity of cell types (e.g., fibroblasts and macrophages) from different species (e.g., avian and mammalian, including human) suggesting limited cell receptor-specificity as well as the general applicability of these proteins. It may also be possible to target recombinant protein-containing proteoliposomes to specific cell types by including specific receptor-binding proteins in the liposome membrane. In this instance, the receptor-binding protein would confer targeted cell attachment of the liposome followed by subsequent enhanced liposome-cell fusion mediated by the recombinant protein.

The demonstrated ability of the p14 ectodomain/p15 endodomain recombinant protein to induce cell-cell fusion indicates their potential use in the production of heterokaryons, for example, the generation of hybridomas for monoclonal antibody production. The induction of cell-cell fusion is usually triggered using the chemical fusogen polyethylene glycol (PEG). Although this procedure does trigger cell-cell fusion, toxic effects on cells hamper the efficiency of heterokaryon isolation. It is generally believed that "natural" membrane fusion is mediated by protein-lipid interactions, therefore, protein-mediated membrane fusion is likely to be much less cytotoxic than chemically-induced cell fusion.

The demonstrated ability of the recombinant proteins to promote efficient cell-cell fusion indicates their potential use as alternatives to chemical-induced cell fusion.

Expression of recombinant proteins in one population of cells, under the control of a strong inducible promoter, could trigger fusion with a second cell population, resulting in decreased cytotoxicity and more efficient heterokaryon isolation. It is contemplated that the recombinant proteins of the invention could be added to cells in the presence of a lipid carrier, such as Lipofectamine™, and induce cell-cell fusion and heterokaryon formation.

The recombinant proteins described herein represent alternatives to the use of enveloped virus fusion proteins in the protein-mediated enhancement of liposome-cell fusion for the intracellular delivery of bioactive molecules. The potential advantages of the p14 ectodomain/p15 endodomain recombinant proteins relate to their unique ability to more strongly fuse to other cells compared to native reovirus proteins. The large size, post-translational glycosylation, and complex tertiary structure of the enveloped virus fusion proteins makes synthesis and purification of the functional protein using recombinant DNA approaches and prokaryotic or eukaryotic expression systems problematic.

The majority of studies relating to the use of enveloped virus fusion proteins in proteoliposomes involve the production of virus particles which are subsequently purified, solubilized with detergent, and the viral envelopes containing the fusion protein are reconstituted into "virosomes" by removal of the detergent [see Grimaldi in *Res. Virol.*, 146: 289-293 (1995) and Ramani et al., *FEBS Lett.*, 404:164-168 (1997)].

Unlike most of the enveloped virus fusion proteins, the reovirus fusion proteins, from which the recombinant proteins are derived, are small membrane proteins. Their small size and simple domain organization suggests that these proteins will be easier and more economical to produce in a functional form using a diversity of expression and purification protocols. It is also likely that the small size of the recombinant proteins contributes to less complex protein folding pathways and tertiary structure required for correct protein conformation. As a result, an increased diversity of extraction and solubilization procedures (e.g., choice of detergents and denaturants) should be available to facilitate purification of the functional fusion protein and incorporation into liposomes.

The attractive biological properties of the recombinant proteins relate to their pH-independent fusion mechanism with numerous cell types. The recombinant proteins function at neutral pH, unlike the influenza virus HA protein, simplifying their use in cell culture and in vivo under physiological conditions. Furthermore, the recombinant proteins fuse numerous types of cells suggesting their broad applicability as fusogens. This could include such primary cell types as dendritic cells, neurons, and stem cells which are difficult to transfect using standard transfection reagents.

Accordingly, the p14 ectodomain/p15 endodomain recombinant proteins could be used to promote liposome-cell fusion and the efficient intracellular delivery of DNA or other bioactive compounds into a diversity of cultured cell types, primary cell cultures, tissue explants, or in vivo.

In order to use recombinant proteins for heterokaryon production, the proteins will need to be expressed in a controlled, inducible manner from within cells using standard recombinant DNA approaches. The utility of this approach has already been demonstrated in homologous cell-cell fusion in a non-inducible manner. In a similar fashion, these proteins can promote cell-cell fusion between heterologous cell types in an inducible manner.

The development of recombinant proteins for enhanced liposome-cell fusion requires the expression and purification of the functional fusion proteins and their incorporation into liposome membranes to produce proteoliposomes. The recombinant proteins can be expressed and purified using standard procedures. Expression can be accomplished employing a variety of expression systems, e.g., baculovirus or yeast eukaryotic expression vectors or from prokaryotic expression vectors, depending on expression levels and functional activity of the protein. Various detergent extraction procedures can be used to solubilize the proteins, which can then be purified as detergent-protein complexes using standard protein purification protocols. The proteins are readily soluble in various detergents (e.g., 0.8% Triton™ X100, 0.8% NP40, 0.8% octylglucoside) increasing the diversity of approaches available for functional protein purification. The small size of the recombinant proteins suggests that protein solubilization and purification should be considerably more simple than similar approaches to purify larger, more complex membrane proteins.

Figure 4A:
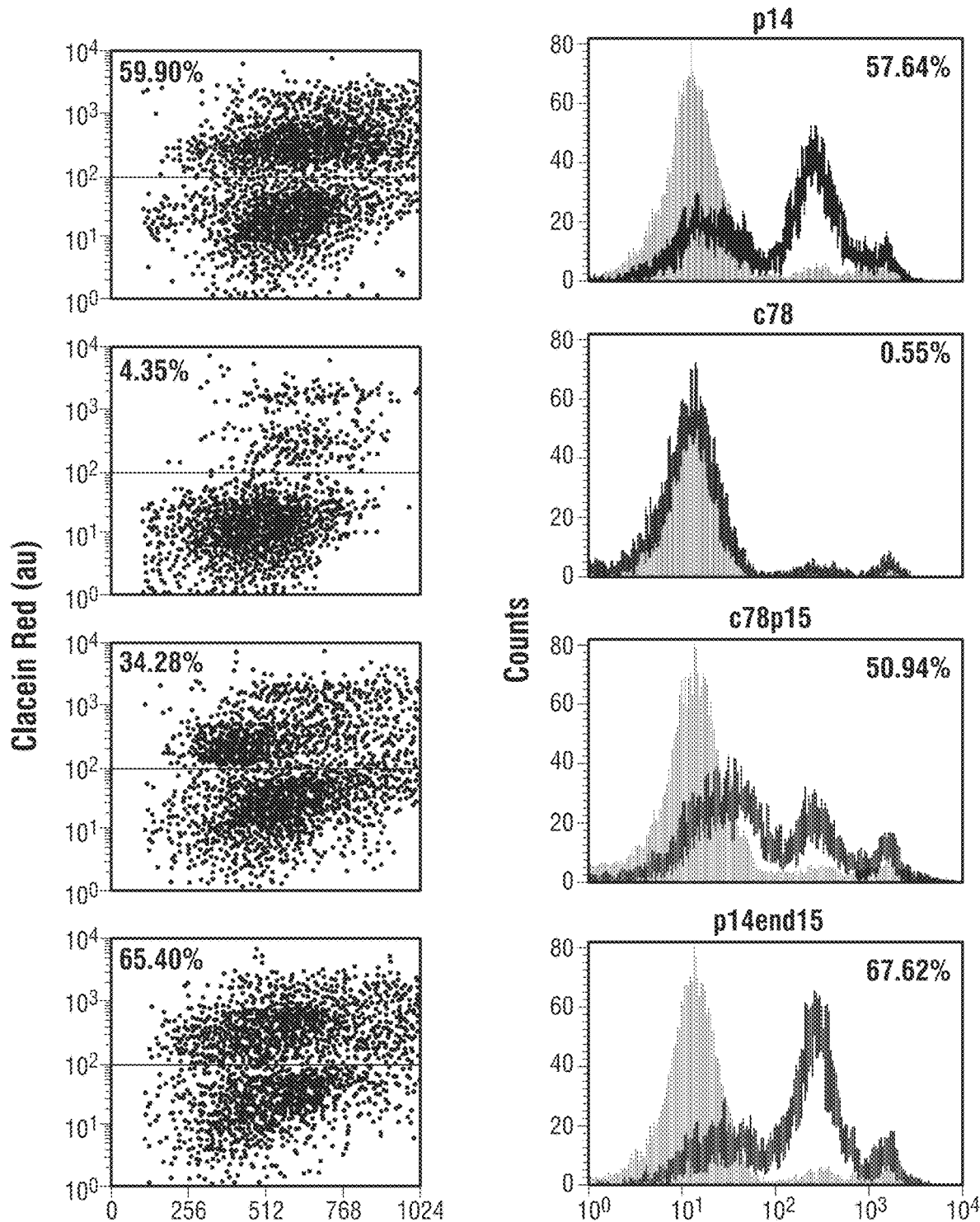
FIG. 4A, FIG. 4B, and FIG. 4C is a graphical representation showing (FIG. 4A) the extent of pore formation as determined by co-transfection of eGFP with empty pcDNA3 vector (not shown), p14, c78, c78e15 and p14end15 at a 1:14 ratio. Representative dot plots (left) and histograms (right) are shown from the same experiment, done in triplicate.
Figure 4B:
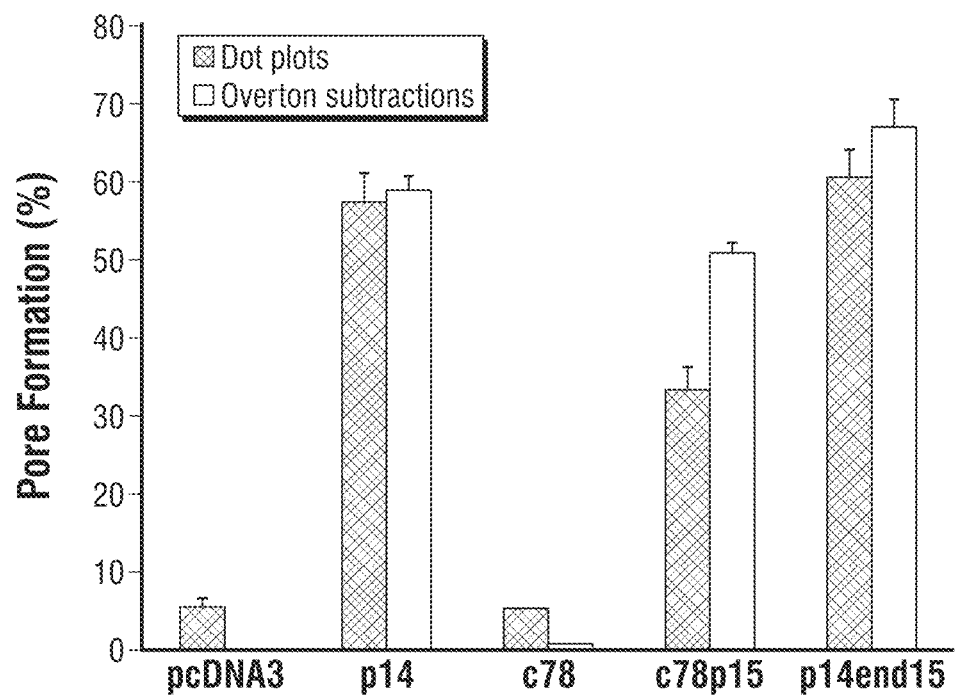
Figure 4C:
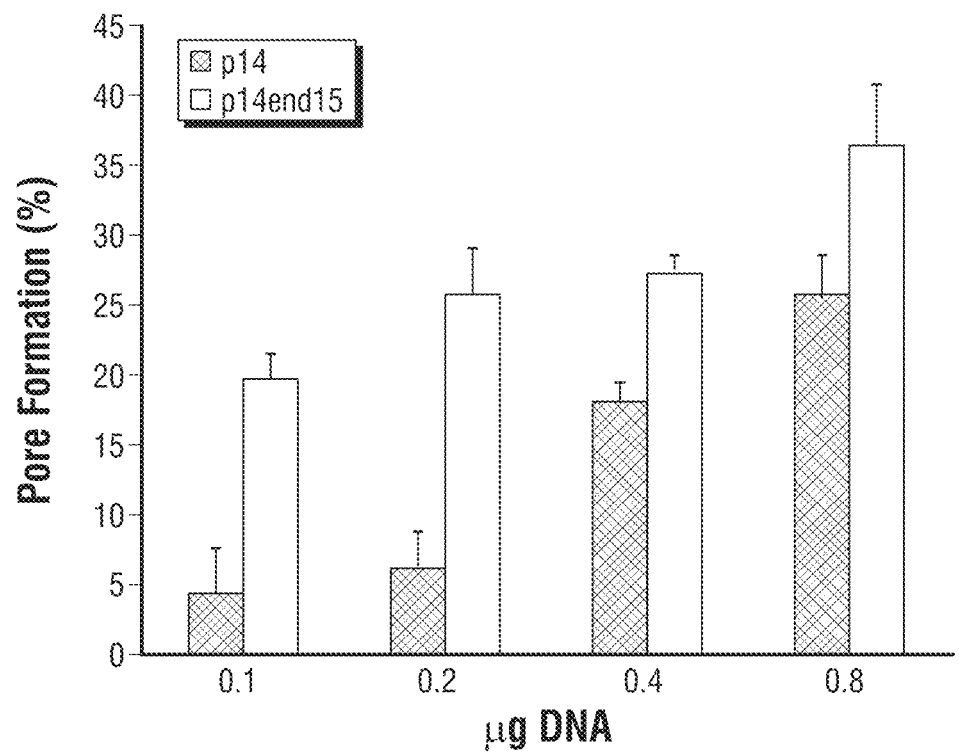

The detergent-protein complexes can be mixed with lipids and the detergent removed by dialysis, chromatography, or extraction according to standard published procedures, similar to methods used to generate influenza HA or Sendai virus F protein-containing virosomes (see Grimaldi, Res Virol, 146: 289-293, 1995 and Ramani et al., FEBS Lett, 404: 164-168, 1997). These procedures will result in the production of proteoliposomes, lipid vesicles containing the ARV, NBV, or BRV fusion proteins embedded in the vesicle membrane. Once again, optimal conditions for proteoliposome production can be empirically determined as can the lipid composition and size of the proteoliposomes, which can affect the efficiency of liposome-cell fusion. Bioactive molecules of interest (e.g., nucleic acids, proteins or peptides, pharmacological compounds, and the like) can be included during the formation of the proteoliposmes to facilitate packaging of the molecule within the liposomes. The proteoliposomes can be purified by centrifugation and used to deliver bioactive molecules intracellularly, either in cell culture or in vivo, by protein-enhanced fusion of the proteoliposomes with cell membranes.

The present invention has been described with regard to one or more embodiments. However, it will be apparent to persons skilled in the art that a number of variations and modifications can be made without departing from the scope of the invention as defined by the claims.

Example 1: The p15 Endodomain Functions Modularly to Enhance Membrane Fusion Construct c78 is a truncation mutant in which 47 residues were deleted from the p14 C-terminus (Corcoran and Duncan, *J. Virol.,* 78(8):4342-51, 2004). As shown in FIG. 2, the c78p15 construct is a re-extension of c78, in which the length of the cytoplasmic tail has been restored to 125 residues using heterologous sequence corresponding to the last 47 residues (93 to 140) of the p15 endodomain. These 47 C-terminal residues are downstream of the p15 HP and thus the p15 HP is not included in the c78p15 chimeric construct. In agreement with earlier findings (Corcoran and Duncan, *J. Virol.,* 78(8):4342-51, 2004), when a QM5 monolayer was transfected with the p14 truncation mutant (c78), a loss of fusion activity was observed by syncytial indexing (FIG. 3). When cells were transfected with the re-extension construct c78p15 however, syncytia formation was restored to authentic p14 levels (FIG. 3). In addition to these truncation constructs, cells were also transfected with a chimeric construct, p14end15, in which the entire endodomain of p14 was replaced by that of p15 (FIG. 3). In contrast to c78p15, the p14end15 construct included the p15 HP resulting in a chimera with two HPs; the exoplasmic HP of p14 and the cytoplasmic HP of p15.

When used to transfect a QM5 monolayer, the p14end15 construct induced syncytia formation to an extent that was greater than that of wild type p14 (FIG. 3).

To determine if syncytia formation correlated with pore formation, plasmids encoding authentic p14, c78, c78p15, p14end15 or the empty pcDNA3 vector were cotransfected into QM5 cells with the eGFP expression plasmid and incubated to allow initial expression. At 3 hours post-transfection, the transfected donor cells were overlaid with target Vero cells pre-labelled with aqueous calcein red dye. Cells were co-incubated to allow for fusion then analyzed by flow cytometry for the transfer of calcein dye to GFP-expressing cells. Uptake of calcein dye was clearly detected in all transfected wells with the exception of the pcDNA3- and c78-transfected wells. The c78p15 construct, which induced syncytia formation to the same extent as wild type p14, also induced pore formation to just slightly less that of p14 when analyzed by dot plot (FIG. 4A and FIG. 4B). When the same samples were analyzed by Overton subtractions however, c78p15 was found to induce pore formation to approximately the same extent as authentic p14 (FIG. 4B). Since p14end15-transfected cells fuse so extensively, the lower levels of pore formation detected relative to the syncytial index may be due to a masking effect resulting from saturation of the assay detection limits. To test this hypothesis, the amount of p14end15 or p14 expression plasmids co-transfected into donor cells was titrated in two-fold increments, down to one eighth the amount transfected in panel B (FIG. 4C). Plasmid titration corresponded to a decrease in fusion and unmasked the p14end15 fusion enhancement, revealing a clear increase in fusion induced by p14end15 relative to p14 under less fusogenic conditions (FIG. 4C).

Example 2: The p15 Endodomain does not Alter Protein Expression Levels at the Cell Surface The FAST protein endodomains have recently been implicated a having a role in trafficking to the plasma membrane. Reduction in the levels of protein expressed on the cell surface are known to correlate to lower syncytial indexes. Based upon these observations, experiments were conducted to determine if the increased fusogenicity of p14end15 was due to enhanced trafficking to the cell surface.

When comparing the surface levels of proteins in cells that have fused to varying extents, syncytia formation may theoretically result in an increased level of surface expression compared to non-fused cells due to an increase in the amount of translation machinery. Therefore, to directly compare surface expression levels between constructs, their fusion activity must be abolished to relieve the bias from syncytia formation. In the case of constructs containing the ectodomain of p14, fusion can be inhibited using low dilutions of the anti-p14ecto antibody (FIG. 5A). Live monolayers are then stained with a fluorescence-conjugated secondary antibody and surface expression can be quantified by flow cytometry. This approach was used in an attempt to compare the levels of p14, c78, c78p15 and p14end15 present in the plasma membrane. While addition of the anti-p14ecto antibody inhibited fusion mediated by p14 and c78p15 (data not shown), it was insufficient to completely inhibit fusion mediated by p14end15 (FIG. 5B). Although, antibody inhibition and subsequent surface staining did reveal that c78p15 was expressed on the cell surface to a greater extent than authentic p14 (FIG. 5C). As such, increased surface expression levels may not always result in a corresponding increase in fusion.

To determine if p14end15 was present on the cell surface to the same extent as wild type p14, a G2A substitution was made in the ectodomain which prevents N-terminal myristoylation. This mutation has been previously shown to eliminate p14-mediated fusion activity without affecting surface levels (Corcoran and Duncan, *J. Virol.*, 78:4342-4351, 2004). To measure surface levels of p14end15, QM5, monolayers were co-transfected with empty pcDNA3 vector and the non-fusogenic p14G2A or p14end15G2A constructs (FIG. 5D). The amount of DNA used for transfection was titrated to correspond to the amounts used in the determination of p14end15-induced pore formation (FIG. 4C). While p14end15 appeared to be present on the cell surface at slightly higher levels than authentic p14 at the highest titration dose, surface levels equalized with decreasing DNA dose (FIG. 5D).

At these lower transfection volumes, the greatest difference in fusion activity between p14 and p14end15 could be observed. Therefore, the fusion potentiating activity of the p15 endodomain in the p14end15 construct is likely due to a true enhancement of fusion enhancement, not an increase in cell surface protein levels.

Example 3: The p15 Endodomain can Rescue Fusion Defects in the p14 Ectodomain

Figure 5A:
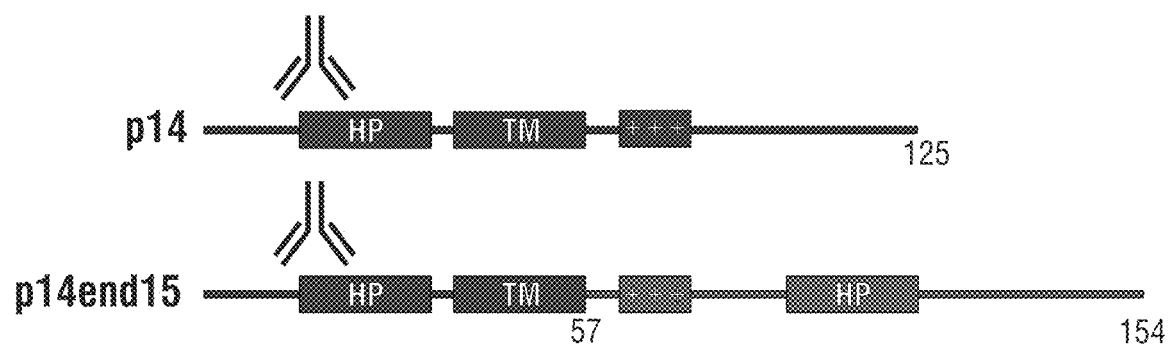
FIG. 5A, FIG. 5B, FIG. 5C, and FIG. 5D are graphical representations showing (FIG. 5A) the locations of binding of the anti-p14ecto antibody to the ectodomains of both p14 and p14end15.
Figure 5B:
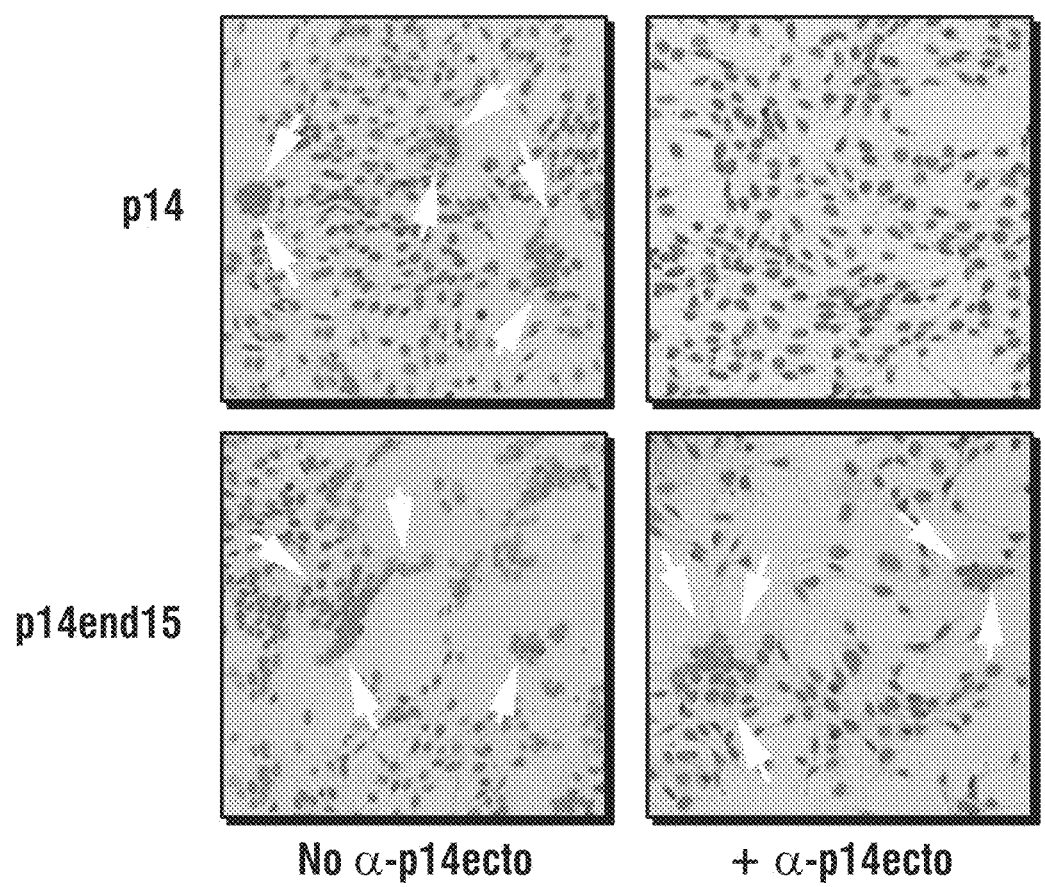
Figure 5C:
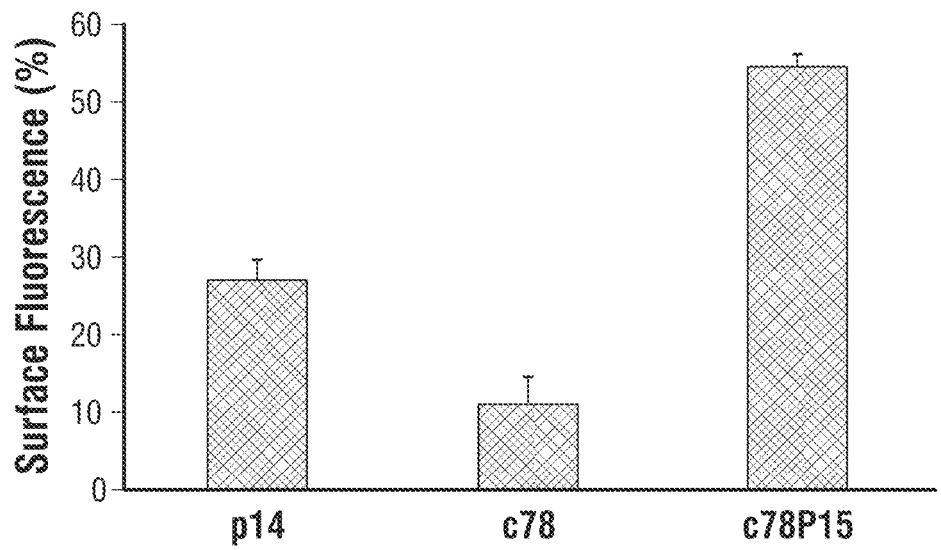
Figure 5D:
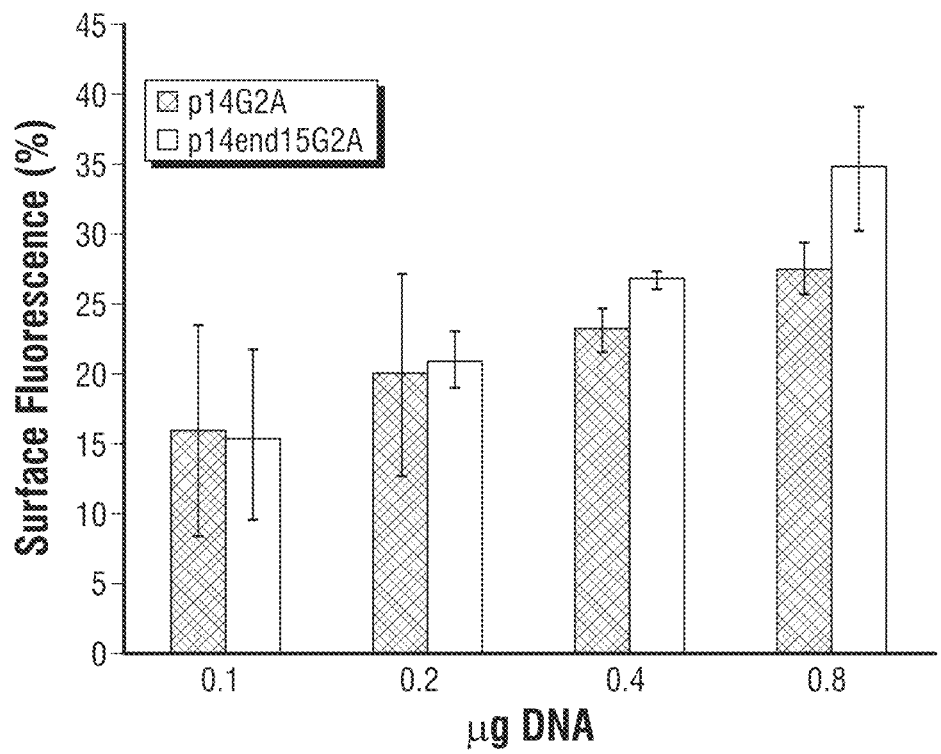
Figure 7A:
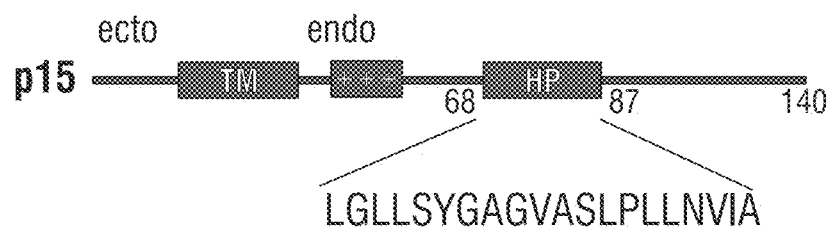
(FIG. 7A) is a schematic representation of the p15 protein indicating the location and sequence of the HP, spanning residues 68-87, inclusive. "ecto" represents ectodomain, "TM" represents transmembrane domain, "endo" represents "endodomain", "+++" represents polybasic region and "HP" represents hydrophobic patch (SEQ ID NO: 8)
Figure 7B:
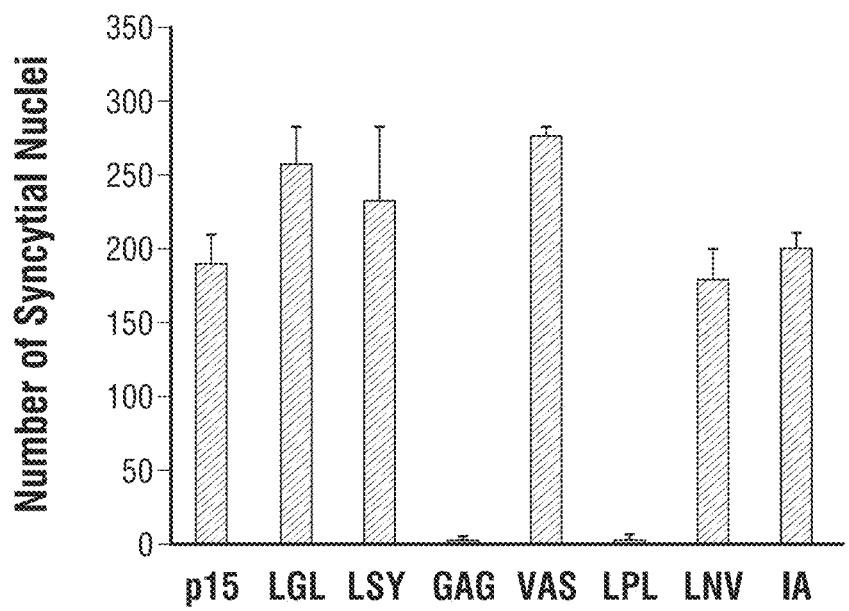
(FIG. 7B) is a graphical representation of QM5 cells transfected with p15 or the HP scan mutants and the average number of syncytial nuclei per field as determined from Giesma stained monolayers 8 hours post-transfection. The residues substituted by alanines in each construct are indicated. Results are expressed as means±standard error of an experiment done three times in triplicate.
Figure 7C:
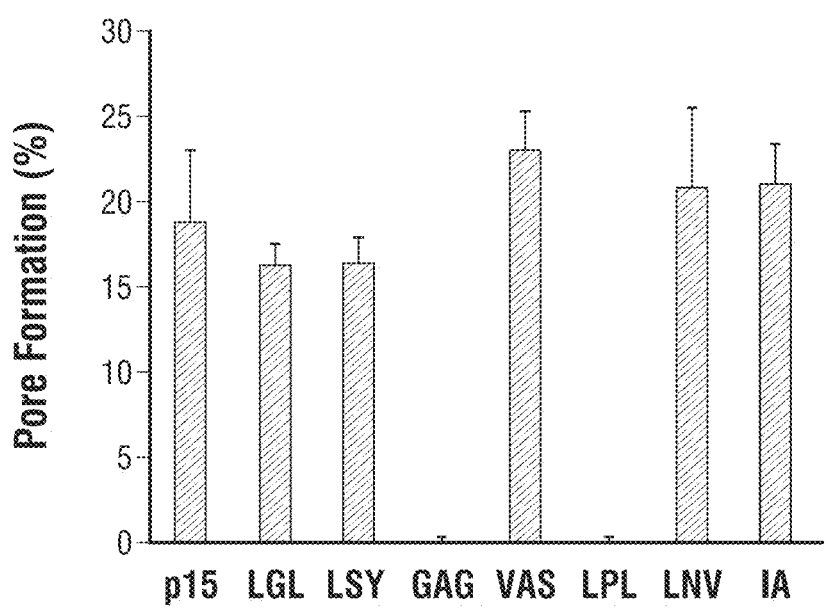
(FIG. 7C) is a graphical representation showing the extent of pore formation determined by co-transfection of GFP with p15 or the alanine scan constructs at a 1:4 ratio. 10,000 gated cells were counted and the percentage of GFP positive cells staining red is indicated. Results are shown as means±standard deviation of Overton subtractions obtained from two pooled experiments done in duplicate.
Figure 8A:
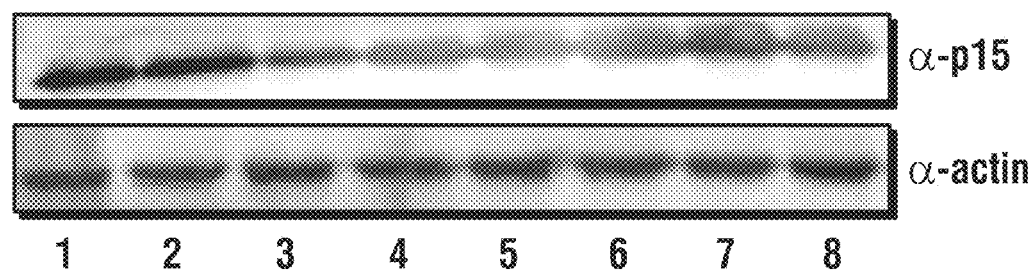
(FIG. 8A) is an immunoblot showing relative expression of p15 HP alanine scan mutants of lysates from transfected QM5 cells. Lane 1-p15, lane 2-p15HP-LGL, lane 3-p15-LSY, lane 4-p15-GAG, lane 5-p15-VAS, lane 6-p15-LPL, lane 7-p15-LNV and lane 8-p15-1A.
Figure 8B:
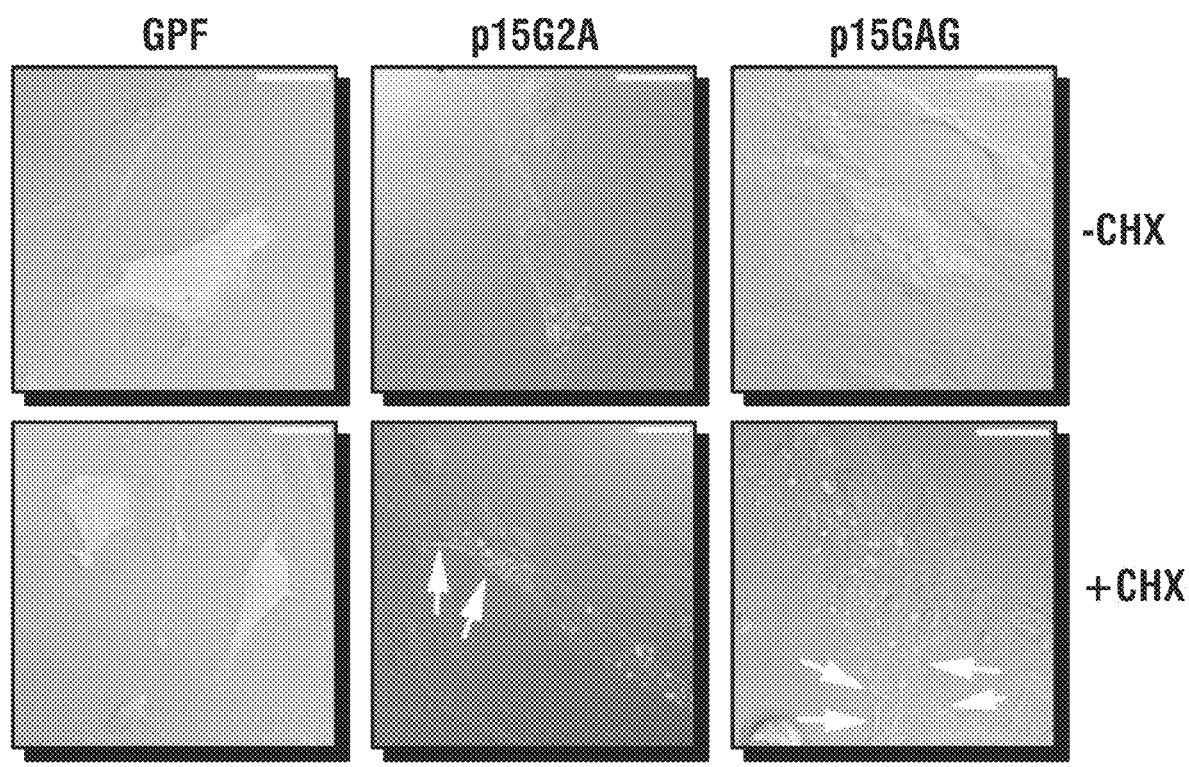
(FIG. 8B) shows QM5 cells transfected with C-terminally GFP-tagged p15G2A, p15-GAG or p15-LPL (not shown) or GFP as a soluble control, and chased to the cell surface with a 3 hour cycloheximide treatment (200 μg/mL), 20 hours post-transfection. Arrows indicate regions of the plasma membrane in which protein has accumulated.

The anti-p14ecto antibody was raised against residues 1 to 36 of the authentic p14 ectodomain and the p14 HP occupies residues 1-21 of the ectodomain (FIG. 5A). As shown in FIG. 5B, incubation with anti-p14ecto antibody prevents syncytia formation in QM5 cells transfected with p14. Conversely, when QM5 cells transfected with the p14end15 construct were incubated with anti-p14ecto antibody, syncytia formation still occurred. Levels of fusion are less than those induced by p14end15 in the absence of the antibody.

Figure 9A:
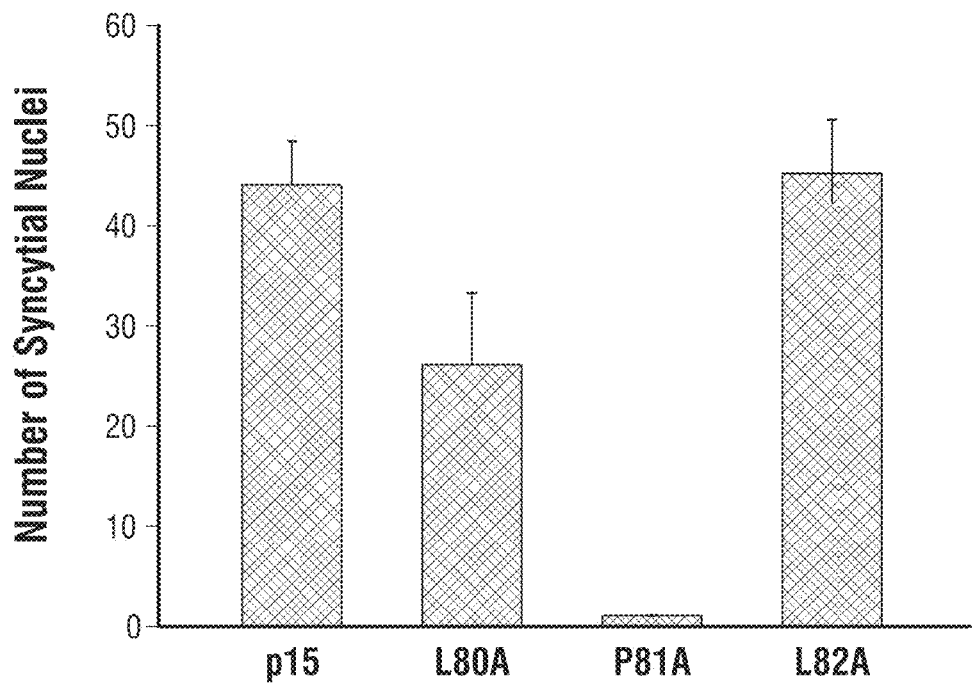
FIG. 9A and FIG. 9B are graphical representations showing (FIG. 9A) QM5 cells transfected with p15, p15L80A, p15P81A or p15L82A. Results are expressed as means±standard deviation of a representative experiment done in triplicate.
Figure 9B:
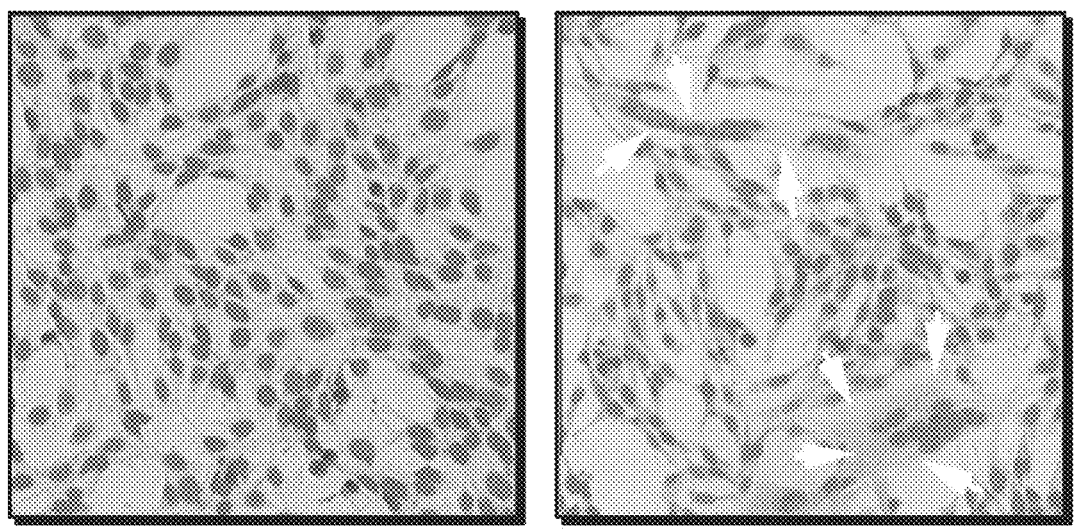

The ability of p14end15 to overcome antibody inhibition also suggests that the motifs present in the p15 endodomain may be able to rescue fusion defects in the p14 ectodomain. Accordingly, the endV9T construct was created in which a V9T substitution was made in the ectodomain HP of p14end15 (FIG. 6A). The V9T substitution was previously found to completely abrogate the ability of authentic p14 to induce syncytia formation (Corcoran et al., *J Biol. Chem.*, 279(49):51386-94, 2004). As was the case with antibody inhibition, the V9T substitution did not result in a loss of syncytia formation in a p14end15 backbone but did eliminate syncytiogenesis in a p14 backbone (FIG. 6B).

While p14V9T is non-fusogenic by syncytial indexing, when QM5 monolayers were co-transfected with GFP and p14V9T or endV9T then co-incubated with calcein-labelled target Vero cells to measure the extent of pore formation induced by these constructs, low levels of pore formation mediated by p14V9T were detectable by Overton subtraction, and to a lesser extent by dot plot analysis (FIG. 6C). The endV9T construct mediated pore formation to a greater extent than p14V9T when analyzed by either dot plot or histogram subtraction, supporting results obtained by Giemsa staining of transfected monolayers and suggesting that the p15 endodomain may either enhance pore formation or stabilize the formation of fusion pores mediated by p14V9T.

A G2A substitution was generated in the p14end15 ectodomain, which prevents myristoylation. This substitution does inhibit p14end15-mediated fusion (data not shown). This is in agreement with the observation that a G2A substitution in the ectodomains of both p14 and p15 abrogates their fusion activity. Therefore, while the p15 endodomain is able to overcome defects in the HP of the p14 ectodomain, N-terminal myristoylation still appears to be a requirement for p14end15-mediated fusion.

Example 4: Glycine and Proline Residues in the p15 HP are Involved in Fusion Activity To determine if the p15 HP plays an enhancing role in the p14end15-mediated fusion reaction, an alanine scan of the HP was first carried out in the context of a wild type p15 backbone to identify residues involved in p15-mediated fusion (FIG. 7A). The residues of the p15 HP were substituted, three at a time, with alanine residues. Where alanine was the naturally encoded residue (as is the case with the p15-GAG construct, for example), the alanine residue was maintained and not replaced with a heterologous amino acid. By syncytial indexing of transfected QM5 monolayers, two regions of the HP were identified to be involved in p15-mediated fusion (FIG. 7B). The p15 HP alanine scan mutants p15-GAG and p15-LPL were both found to be non-fusogenic by syncytial indexing. This phenotype was next confirmed using the fluorescence-based pore formation assay described above and both mutants were also found to be deficient in their ability to promote the formation of fusion pores (FIG. 7C).

When the presence of each mutant was tested in the lysates of transfected QM5 cells by SDS-PAGE analysis and Western blotting, all seven alanine scan mutants could be detected. Equal amounts of lysates, based on total protein concentration, were loaded (FIG. 8A). With approximately equal amounts of actin, present in each sample as a loading control, both authentic p15 and p15-LGL (lanes 1 and 2, respectively) may have slightly elevated overall steady-state protein levels relative to the other alanine scan mutants. However, both non-fusogenic mutants, p15-GAG and p15-LPL, were clearly expressed in transfected lysates to approximately the same extent as the other alanine scan mutants, which showed no fusion defects. In some instances, mutations of glycine and proline residues in fusion peptides can cause trafficking defects (Levy-Mintz and Kielian, *J. Virol.,* 65(8):4292-300, 1991; Shome and Kielian, Virology, 279(1):146-60, 2001), though these domains are found in the ectodomains of enveloped viral fusion proteins.

In addition, regions in the cytoplasmic domains of the FAST proteins have been identified as being important for trafficking to the plasma membrane. To determine if the GAG or LPL alanine substitutions resulted in a trafficking defect, p15G2A, p15-GAG and p15-LPL were C-terminally tagged with GFP and their presence on the surface of transfected cells was detected. Cycloheximide was used to stop translation and deplete the intracellular pool of p15, chasing already translated proteins to the cell surface (FIG. 8B). While p15 and the p15 alanine scan constructs were both chased to the surface (p15 and p15-GAG shown), cycloheximide treatment had no effect on cells expressing GFP (FIG. 8B). Taken together, these observations indicate that the loss of fusion activity observed in cells transfected with p15-GAG and p15-LPL is not due to a trafficking defect.

Since the alanine scan was conducted by substituting the HP residues in the authentic p15 sequence in groups of three, experiments were conducted to determine which of the three substituted residues of p15-LPL were required for fusion activity. Single alanine substitutions were made of the leucine and proline residues at positions 80-82 in the wild type p15 sequence to create p15L80A, p15P81A and p15L82A. QM5 cells were transfected with each point substitution construct and a syncytial index was taken at 8 hours post-transfection (FIG. 9A). While the L80A point substitution resulted in a limited loss of fusion activity relative to wild type p15, p15L82A retained full fusion activity. In contrast to the leucine point substitutions, no syncytia were formed in p15P81A-transfected monolayers at 8 hours post-transfection (FIG. 9A). However, if transfected cells are incubated under growth conditions for 24 hours, limited p15P81A-induced syncytia formation could be observed (FIG. 9B).

Example 5: A Peptide Corresponding to the p15 HP Induces Liposome-Liposome Lipid Mixing To determine if the p15 HP has inherent membrane destabilizing properties, the ability of a peptide corresponding to this region to induce lipid mixing was investigated using a fluorescence resonance energy transfer (FRET) liposome-liposome lipid mixing assay.

Non-fluorescent liposomes and fluorescent liposomes composed of DOPC:DOPE:Chol at a 1:1:1 molar lipid ratio were mixed with peptides and fusion was monitored as a loss of FRET and corresponding increase in fluorescence measured by fluorimetry. In the fluorescent liposome composition, 4% DOPE was replaced with 2% Rhodamine(Rho) DOPE and 2% NBD-DOPE. In addition to the sequence corresponding to the authentic p15 HP sequence (p15HP), the previously described p14myr+ and p14myr– were used as positive and negative controls for lipid mixing, respectively (FIG. 10A). When added to the liposome mixture, 50 µM p15HP induced extensive lipid mixing greater than that induced by equal concentrations of p14myr+. As expected, the p14myr– peptide did not induce lipid mixing above background DMSO alone levels (FIG. 10B). When decreasing amounts of p15HP peptide were added to liposomes a dose-response in lipid mixing was observed (FIG. 10C). Interestingly, when a scrambled version of the p15HP peptide, p15HPscr (FIG. 10A) was added to liposomes, this peptide also induced a substantial loss of FRET (FIG. 10D). However, the increase of fluorescence was not stable and the ability of the peptide to induce lipid mixing was not dose-dependent (FIG. 10D). Visually, addition of p15HPscr to liposomes resulted in increased turbidity of the sample which may represent the formation of liposome or peptide aggregates (data not shown). Since p15HPscr-induced loss of FRET did not appear to be dose-dependent it is possible that it resulted from a non-specific interaction of p15HPscr with liposomes. It is evident however, that the sequence of the p15 HP has membrane interaction and destabilization potential above and beyond that of the p14 ectodomain, which contains a fusion peptide.

Example 6: Truncation of the p15 TMD Eliminates Membrane Fusion Activity

The p14 and p10 TMDs are both predicted to be 19 residues in length while the p15 TMD is predicted to be 23 residues. To determine whether the terminal residues of the extended p15 TMD influence p15-induced membrane fusion, a series of deletions were created in which the p15 TMD was truncated by either one or two residues from the N-terminal end (p15Δ21 and p15Δ21/22, respectively) or four residues from the C-terminal end (p15Δ40-43) (FIG. 11A). Giemsa stains of transfected QM5 monolayers clearly revealed that each deletion of the authentic p15 TMD resulted in the complete loss of syncytiogenesis (FIG. 11B). Generally, when membrane fusion is lost due to insufficient transmembrane length, fusion of these mutants can be recovered by restoring the length of the TMD. The N-terminal isoleucine or isoleucine and valine residues that were deleted from the p15Δ21 and p15Δ21/22 constructs, were therefore replaced with alanine residues to create p15I21A and p15IV21/22A, respectively (FIG. 11A). Replacement of the N terminal residues of the p15 TMD with alanine did not restore membrane fusion activity, with transfected monolayers containing only individual antigen positive cells (FIG. 11C). The cell-cell fusion activity of the p15 FAST protein is therefore sensitive to either truncation or replacement of the terminal residues of the TMD.

Figure 12A:
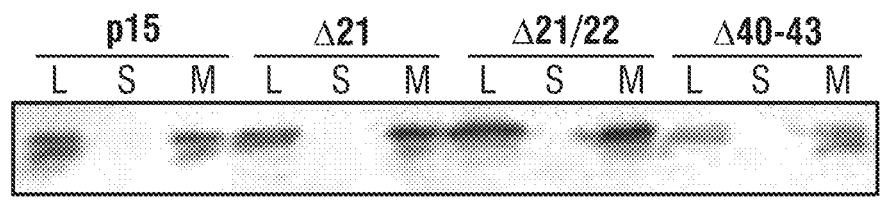
(FIG. 12A) represents transfected QM5 cells lysates (L) were fractionated soluble (S) and membrane (M) fractions by ultracentrifugation. The presence of p15, p15Δ21, p15Δ21/22 or p15Δ40-43 in each fraction was detected by SDS-PAGE and immunoblotting using polyclonal anti-p15 C-terminal antiserum.
Figure 12B:
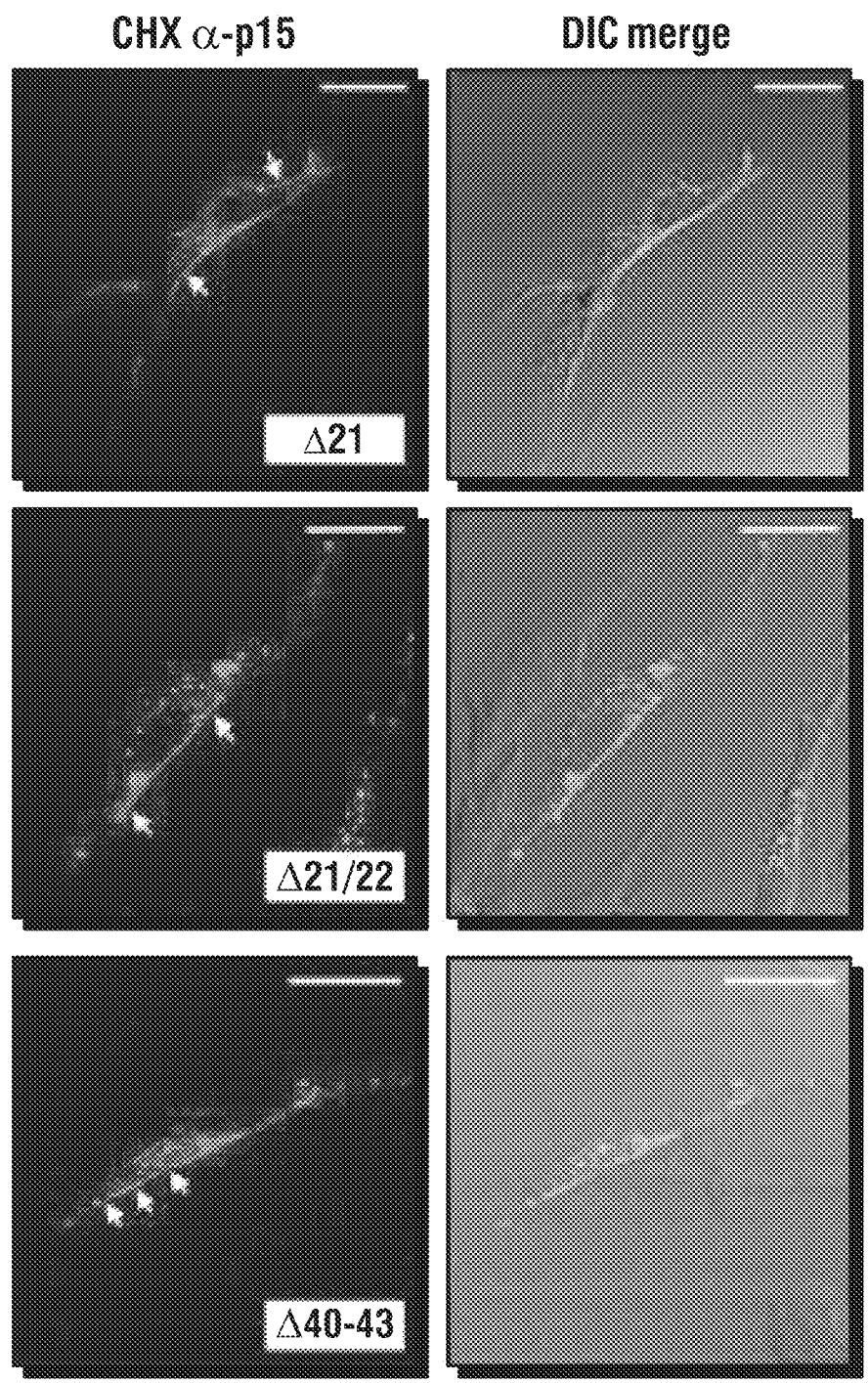
(FIG. 12B) represents QM5 cells were transfected with C-terminally GFP-tagged p15Δ21, p15Δ21/22 or p15Δ40-43 and chased to the cell surface with a 3 hr cycloheximide treatment at 20 h post-transfection, then fixed with formaldehyde. Images shown represent two or three merged fluorescent Z sections (left panels) overlaid on the DIC image (right panels). Arrows indicate plasma membrane-localized p15. Scale bars=20 μm.

The FAST protein TMDs function as reverse signal-anchors to direct co-translational membrane insertion. To determine whether the truncated p15 TMDs could still function as reverse signal-anchors, transfected cell lysates were separated into the cytoplasmic and membrane fractions by high-speed ultracentrifugation. SDS-PAGE analysis and Western blotting using anti-p15 C-terminal antiserum indicated each deletion construct was found exclusively in the pelleted membrane fraction (FIG. 12A), confirming that the truncated TMDs were still capable of directing membrane insertion of p15 as an integral membrane protein. Some viral fusion protein TMD truncation constructs also exhibit trafficking defects. To assess whether truncation of the p15 TMD disrupted trafficking to the plasma membrane, the p15Δ21, p15Δ21/22 and p15Δ40-43 constructs were visualized by confocal immunofluorescent microscopy (FIG. 12B). In the absence of an antiserum that specifically recognizes the p15 ectodomain, the p15 constructs were C-terminally tagged with GFP. To partially deplete intracellular pools of p15 (whose fluorescence intensity masks the fluorescence of plasma membrane localized p15), cells were treated for 3 hrs with cycloheximide to stop translation and allow trafficking of the already translated p15 proteins to the cell surface. A fusion-dead p15G2A myristoylation-minus construct was also employed to allow extended incubations in the absence of syncytium formation to improve detection of plasma-membrane localized p15. The p15G2A mutant traffics to the cell surface to the same extent as wild type p15, and this same procedure was previously used to demonstrate p15 plasma membrane localization. As shown by confocal fluorescence microscopy, a clearly detected ring of fluorescence surrounding transfected cells was evident in cells expressing authentic p15 and all of the truncated p15 TMD constructs (FIG. 12B), indicating truncation of the p15 TMD did not qualitatively interfere with p15 trafficking to the plasma membrane. The p15 TMD therefore specifically influences membrane fusion activity, independent of the role of the TMD as a reverse signal-anchor or any role of the TMD in protein trafficking.

Example 7: The p15 TMD Requires Hydrophobic and β-Branched Residues at the N-Terminus for Fusion The truncation and alanine replacement results indicated the importance of the N-terminal residues of the p15 TMD in membrane fusion activity. In addition to being hydrophobic, the N-terminal residues of the p15 TMD are also β-branched amino acids. β-branched residues have been implicated in the role of TMDs in membrane fusion, which relates to their helix destabilizing activity and appears to be particularly important when these residues are found at terminal positions in a TMD. To determine whether hydrophobicity and/or β-branched residues are required at the N-terminus of the p15 TMD, the terminal residues were substituted with either threonine, a β-branched and hydrophilic residue, or with leucine, a hydrophobic and non-β-branched residue (FIG. 13A). To examine the effect of these substitutions on membrane fusion, the kinetics of syncytium formation were obtained from transfected QM5 monolayers that were fixed and Giemsa-stained from 6-16 hrs post-transfection (FIG. 13B). Authentic p15 rapidly induced cell-cell fusion with the onset of syncytia formation occurring within 4-6 hrs post-transfection. Robust fusion leading to apoptosis and disruption of transfected monolayers induced by the authentic p15 protein precluded the determination of a syncytial index past 8 h post-transfection. Substitutions of the N-terminal isoleucine residue with either threonine or leucine led to dramatic decreases in both the onset and extent of syncytiogenesis (FIG. 13B). At 8 hrs post-transfection, when p15-transfected monolayers were approaching the maximal extent of syncytiogenesis, there was little if any evidence of syncytia in cells transfected with p15I21T or p15I21L. However, syncytia became evident shortly thereafter and continued to develop to significant levels by 16 hrs post-transfection (FIG. 13B). Substitution of both the N-terminal isoleucine and valine residues resulted in a complete loss of syncytium formation (data not shown). The decrease or loss of fusion activity with all of these constructs was not due to decreased expression of the substitution mutants, as determined by SDS-PAGE and Western blotting analysis (FIG. 13C).

Syncytial indexing does not permit the detection of mutants for which fusion is initiated but arrested prematurely at an earlier step, such as hemifusion or pore formation. Numerous studies have implicated the TMDs of enveloped viral proteins in the formation or expansion of stable fusion pores. To determine if the p15 TMD chimeras were capable of inducing the formation of stable fusion pores, a previously described FACS-based pore formation assay was used. QM5 cells were co-transfected with the pEGFP expression plasmid and a plasmid encoding either authentic p15 or a p15 TMD substitution construct, and briefly incubated to allow initial transgene expression. The transfected donor cells were then overlaid with target Vero cells labeled with the aqueous fluor calcein red. Donor and target cells were co-cultured to allow fusion events to occur, then trypsin-treated to generate single cell suspensions that were analyzed by flow cytometry. Quantifying the percentage of GFP27 expressing donor cells that acquired the small 800 Da calcein red fluor from target cells is indicative of stable pore formation. As with syncytium formation, by 9 hrs post-transfection p15-transfected cells had induced extensive pore formation while the p15 constructs containing N-terminal TMD substitutions induced no detectable pore formation above background levels (data not shown). However, extended incubation of the constructs containing single N-terminal TMD substitutions eventually induced pore formation, the extent of which generally paralleled their relative syncytiogenic capabilities, with p15I21T inducing more pore formation than p15I21L (FIG. 13D). The constructs containing double N-terminal substitutions that failed to induce syncytium formation also failed to induce pore formation that exceeded background levels (FIG. 13D). Therefore, replacement of the N-terminal, hydrophobic, β-branched isoleucine and valine residues with either a polar β-branched residue or a hydrophobic non-β-branched residue dramatically impairs or eliminates p15 membrane fusion activity at, or prior to, the pore formation stage of the fusion reaction. Since an alanine substitution of the same residue eliminated p15 fusion activity (FIG. 11C), it is inferred that hydrophobic, β-branched residues at the N-terminus of the p15 TMD contribute to an active role for the TMD in membrane merger.

Figures 14A, 14B:
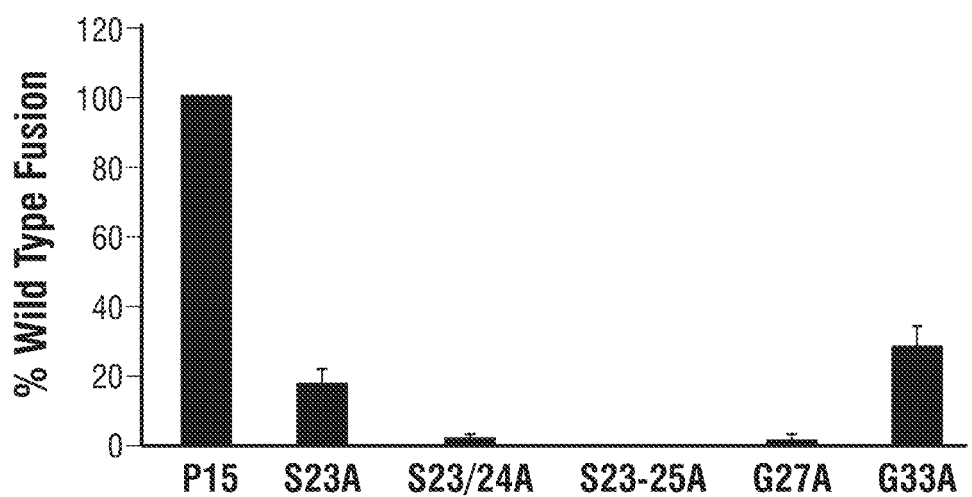
(FIG. 14A) is a linear representation of the TMD of wild-type p15 and the locations of alanine substitutions of the glycine and serine residues in the indicated substitution constructs (SEQ ID NO:11).
(FIG. 14B) is a graphical representation showing the percent syncytium formation relative to authentic p15 at 10 hr post-transfection was determined by comparing the average number of syncytial nuclei per field in Giemsa-stained QM5 monolayers transfected with the indicated glycine and serine point substitutions. Results are the mean±S.D. from a representative experiment done in triplicate.

Example 8: Transmembrane Glycine and Serine Residues are Involved in p15-Mediated Fusion The TMDs of viral fusion proteins generally encode a higher proportion of glycine residues relative to non-fusion proteins. Within the FAST protein family, conflicting results have been found regarding the role of transmembrane glycine residues. The p14 TMD seems to have no primary sequence requirements, whereas the N-terminal half of the ARV p10 TMD contains a triglycine motif that is essential for fusion. The p15 TMD on the other hand, has two glycine residues and a cluster of three serines in the N-terminal half of its TMD. To determine the role, if any, of these p15 TMD motifs, the glycine residues were individually substituted with alanine residues to create p15G27A and p15G33A, and substitutions of the tri-serine motif were also made in which the three serine residues were cumulatively substituted with alanine residues (FIG. 14A). Each construct was transfected into QM5 cells, and the relative fusion capabilities determined by syncytial indexing. Both glycine substitutions had a dramatic effect on membrane fusion; p15G27A produced no visible syncytia at 10 hours post-transfection while the syncytiogenic activity of p15G33A was reduced by ~75% (FIG. 14B). Similarly, replacement of even one serine residue (p15S23A) produced a dramatic decrease in fusion activity and each accumulated substitution (p15S23/24A and p15S23-25A) resulted in a corresponding further decrease and eventual elimination of syncytium formation (FIG. 14B). As discussed above for the N-terminal substitutions, the extent of pore formation mirrored syncytiogenesis; p15G33A 29 induced delayed pore formation that exceeded that induced by p15G27A or p15S23A while multiple substitutions of the tri-serine motif eliminated pore formation (data not shown). Both the transmembrane glycine residues and the tri-serine motif are therefore involved in p15-mediated syncytiogenesis.

Example 9: Construction of the p14-Bombesin Fusion Protein

Figure 15A:
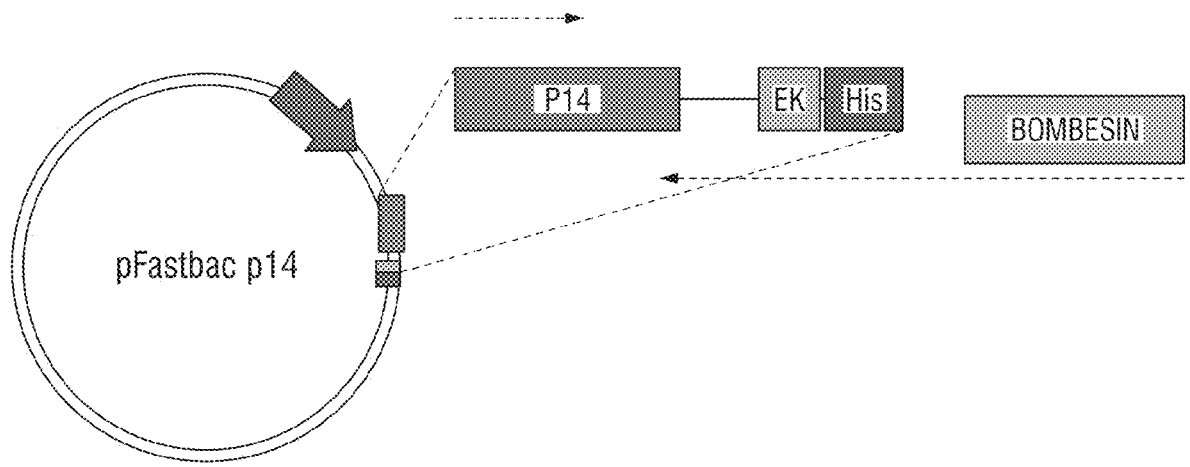
(FIG. 15A) represents a schematic of the pFastBec-p14-bombesin construction.
Figure 15B:
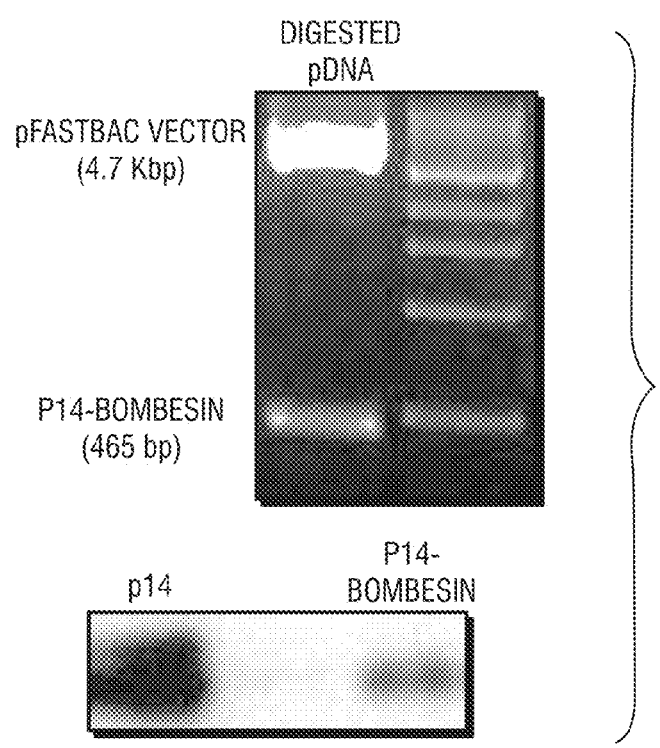
(FIG. 15B) is an immunoblot showing expression of the recombinant virus in sf21 cells and verified protein production.

The p14-Bombesin construct was cloned into the pFastbac vector between BamHI and XhoI (FIG. 15A). For the purposes of being able to determine the utility of the construct to bind to its target, the p14 construct included two tags, namely an enterokinase (EK) cleavage site and 6 histidine residues (His). In practice, the construct need not contain such tags. PCR analysis of the p14-Bombesin construct digested with BamHI and XhoI confirmed that thep14-Bombesin fragment of 465 bp was incorporated into the pFastbac vector (4.8 kbp). A baculovirus expression system was used to produce the recombinant virus in DH10a Bac *E. coli* cells. Expression of the recombinant virus in sf21 cells and verified protein production by Western blot analysis using a polyclonal rabbit p14 primary antibody was confirmed (FIG. 15B). Analysis of the construct confirmed the sequence of the p14-Bombesin fusion polypeptide (FIG. 16).

Example 10: Fusion Activity Assay Using Transfection of Recombinant Plasmid DNA

Figure 17A:
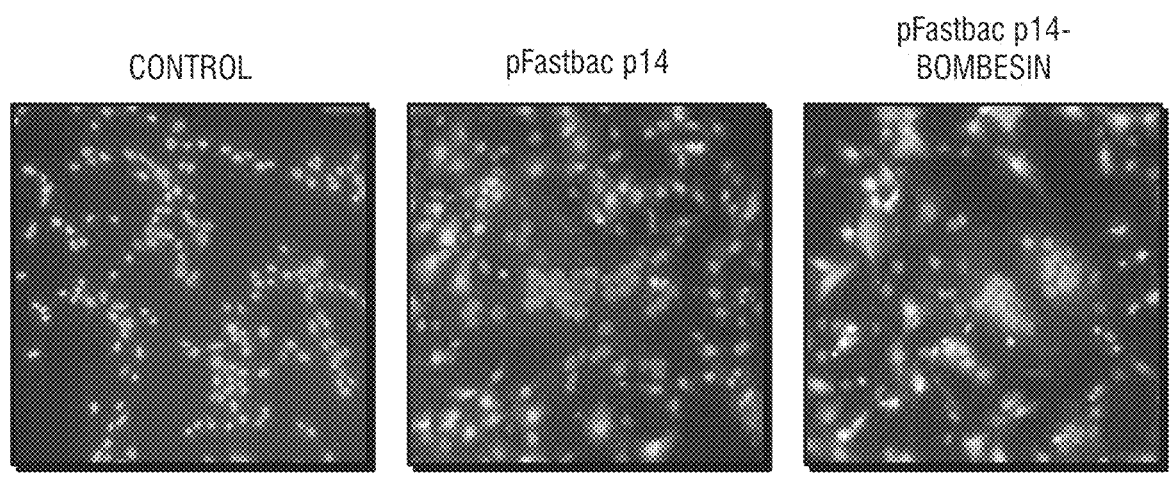
FIG. 17A and FIG. 17B show immunofluorescence images (FIG. 17A) of HT1080 td tomato cells transfected with pFastBac plasmids containing empty vector, p14 or p14-bombesin, and quantitative analysis (FIG. 17B) of syncytia formation using flow cytometry.

HT1080 td tomato cells were transfected with pFastbac plasmids containing either empty vector, p14, or p14-bombesin using Lipofectamine LTX+Plus (FIG. 17A and FIG.

Figure 17B:
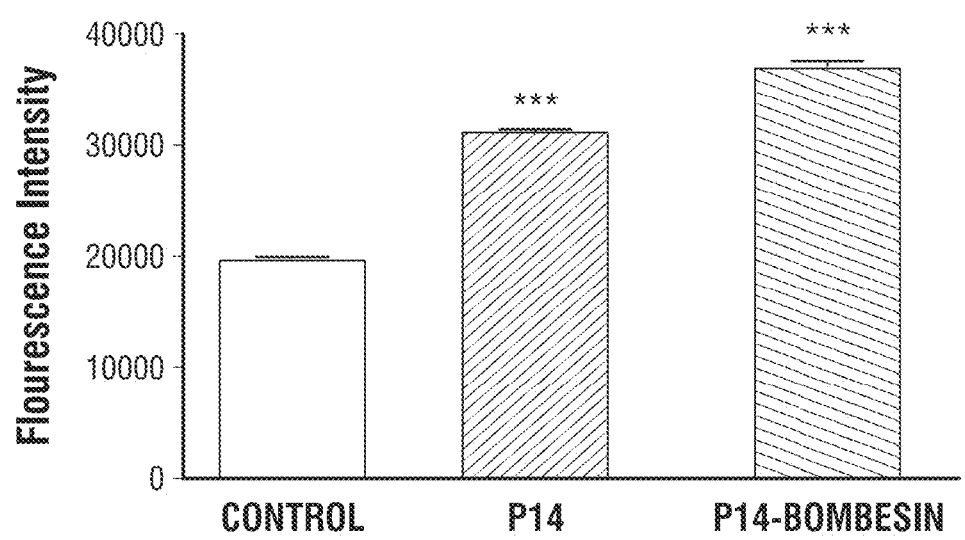

17B). As shown by cells stained red in FIG. 17A, the p14-bombesin construct was taken up and expressed in the HT1080 td tomato cells. Cells were also stained with SYTOX green nuclear stain and then the average number of nuclei per cell was measured using fluorescence intensity (FIG. 17A). The level of syncytia formation indicates that the p14-bombesin construct was as efficient as p14 alone in causing the formation of syncytia (FIG. 17B).

Figure 18:
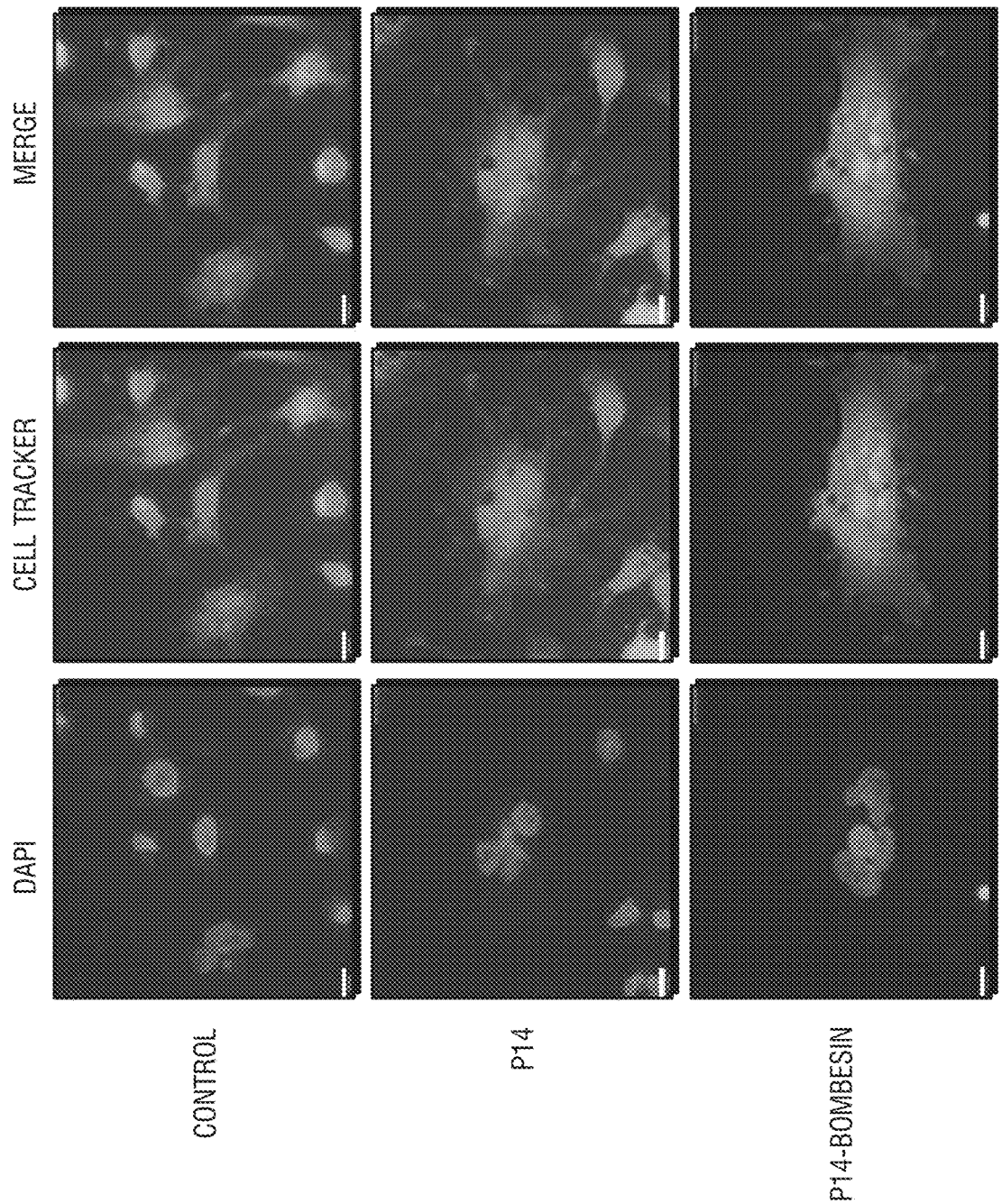
FIG. 18 shows immunofluorescence images of syncytia formation in QM5 quail muscle cells incubated with purified protein (p14 and p14-bombesin). Cells are stained with CellTracker Green and DAPI (blue)

The functionality of the p14-bombesin construct was further confirmed by visualization of syncytia formation in QM5 quail muscle cells (FIG. 18). QM5 quail muscle cells were incubated with purified protein (p14 and p14-bombesin). Syncytia formation can be seen by the formation of multinucleate cells, which are caused by functional p14 proteins.

Example 11: p14-Bombesin Containing Liposomes Target PC-3 Prostate Cells

Figure 19:
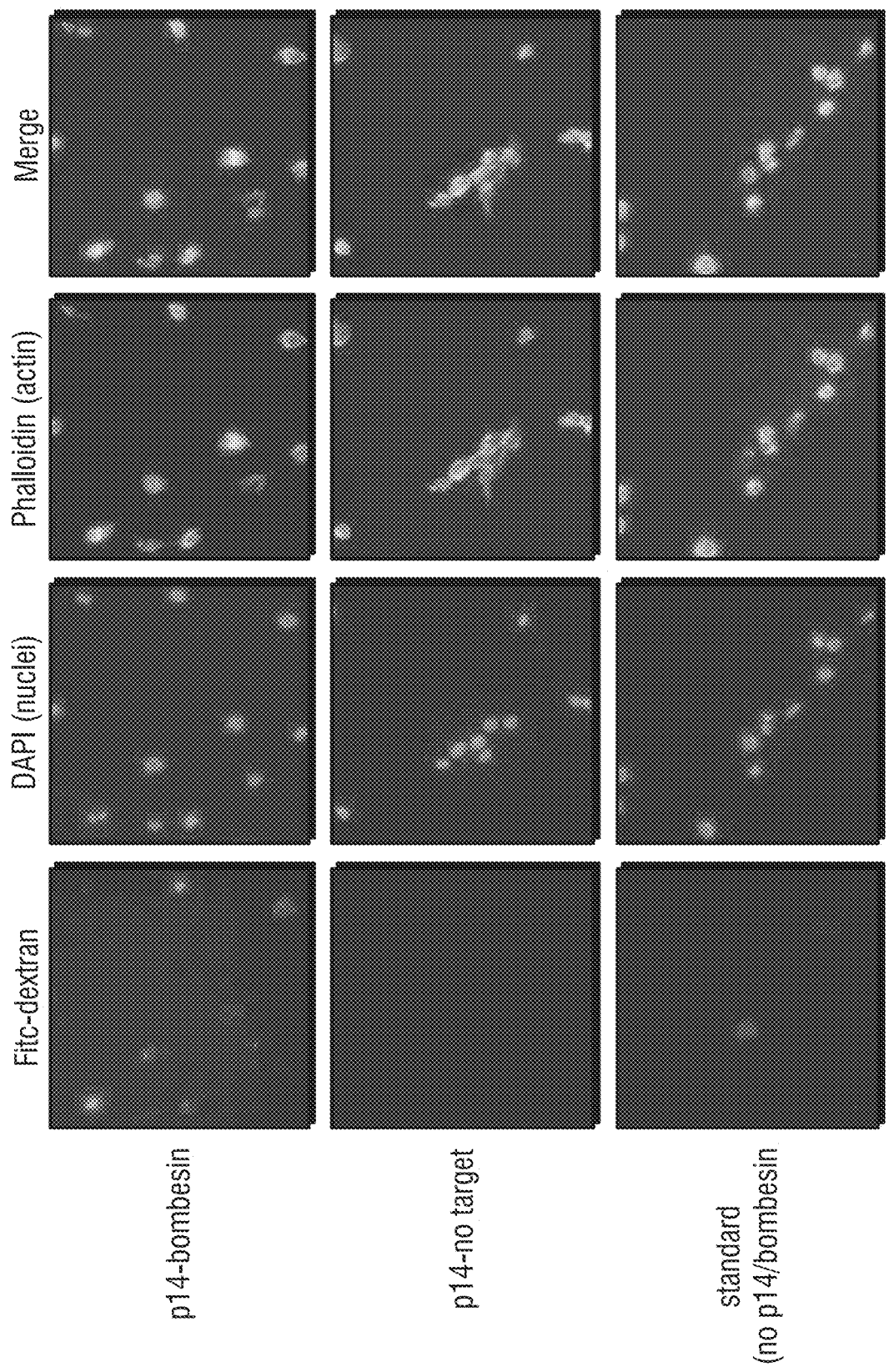
FIG. 19 shows fluorescence imaging of PC-3 prostate cancer cells incubated with liposomes containing FITC-dextran cargo. FITC-dextran (green), DAPI (blue) and actin cytoskeleton (yellow)

PC-3 prostate cancer cells have been previously shown to express the gastrin-releasing peptide receptor (GRP-R). As such, this cell line was used to determine whether the p14-bombesin liposomes could selectively target these cells and delivery their cargo of FITC-dextran (FIG. 19). Liposomes were formulated with no fusion protein, native p14, and p14-bombesin. As shown in the first column of FIG. 19, the p14-bombesin containing liposomes were capable of delivering the FITC-dextran payload to the PC-3 cells.

Figure 20:
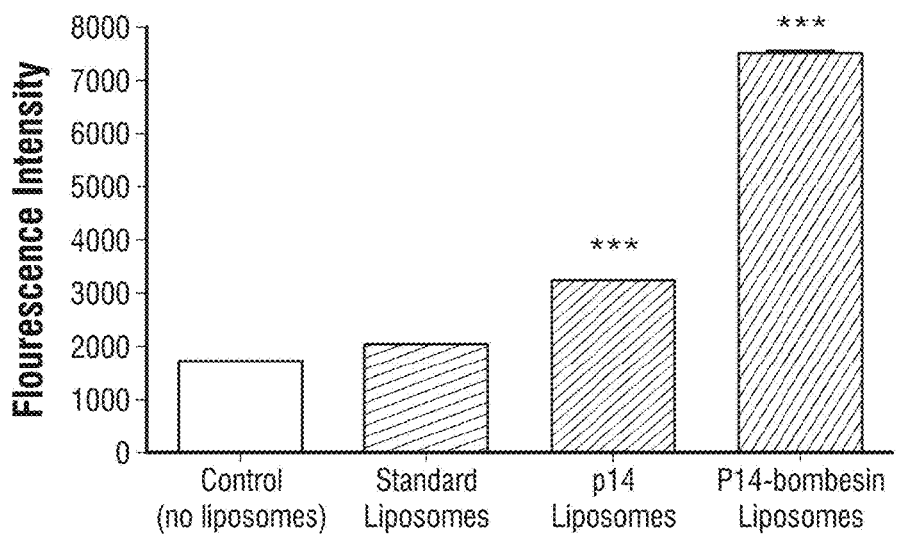
FIG. 20 is a graphical representation of the fluorescence intensity of PC-3 prostate cancer cells exposed to p14-bombesin liposomes containing fluorescent dextran.

Flow cytometry confirmed that indeed the p14-bombesin liposomes were capable of delivering a FITC-dextran payload to PC-3 prostate cells (FIG. 20). Moreover, the amount of FITC-dextran delivered by the p14-bombesin liposomes was more than that of liposomes containing only p14 or liposomes containing no fusogenic proteins.

Example 12: Preparation of Liposomes

Liposomes were prepared following the thin film method of liposome preparation as described by Fenske and Cullis (supra). Briefly, stock lipids based on Table 1 were added to a glass flask with at least three glass beads in the concentrations shown in Table 2. The glass flask containing the lipids in chloroform was attach to a rotary evaporator. The flask was then immersed into attached water bath, preheated to ~38° C. The flask was then rotated at a constant speed. The chloroform was evaporated by vacuum for 1-2 hrs. A predetermined amount of Liposome Buffer (Lip B, 10 mM HEPES (4-(2-hydroxyethyl)-1-piperazineethanesulfonic acid), 150 mM NaCl (sodium chloride), pH 7.4) was added to the flask to generate multilamellar liposomes. The flask was flushed with $N_2$, shaken, and re-flushed with $N_2$. The flask was sealed for 1 hour at room temperature (22-25° C.). This procedure produced a stock of 20 mM multilamellar lipid vesicles.

TABLE 1

| Abbreviation | Chemical Structure | Molecular Formula | Chemical Name |
|---|---|---|---|
| DOPC | 18:1 (Δ9-Cis) | $C_{44}H_{84}NO_8P$ | 1,2-dioleoyl-sn-glycero-3-phosphocholine |
| DOPE | 18:1 (Δ9-Cis) | $C_{41}H_{78}NO_8P$ | 1,2-dioleoyl-sn-glycero-3-phosphoethanolamine |
| PE PEG2000 | 16:0 PEG2000 | $C_{129}H_{259}N_2O_{55}P$ | 1,2-dipalmitoyl-sn-glycero-3-phosphoethanolamine-N-[methoxy(polyethylene glycol)-2000] |
| DOTAP | 18:01 | $C_{42}H_{80}NO_4Cl$ | 1,2-dioleoyl-3-trimethylammonium-propane |
| Cholesterol | cholesterol | $C_{27}H_{46}O$ | cholesterol |
| DC-Cholesterol | cholesterol derivative | $C_{32}H_{57}N_2O_2Cl$ | 3β-[N-(N',N'-dimethylaminoethane)-carbamoyl] cholesterol |

TABLE 2

| | Desired molar ratio (%) | | | | | |
|---|---|---|---|---|---|---|
| Lipids | Standard Profile | Strong Cationic | Extreme Cationic | Extreme Cationic II | Inner Wraposome | Outer Wraposome |
| DOPC | 60 | 30 | 0 | 0 | 0 | 0 |
| DOPE | 30 | 30 | 0 | 25 | 0 | 0 |
| Cholesterol | 4 | 8 | 0 | 0 | 0 | 0 |
| PE-PEG2000 | 0 | 0 | 0 | 0 | 0 | 0.5 |
| DOTAP | 0 | 30 | 100 | 75 | 100 | 99.5 |
| DC-Cholesterol | 6 | 2 | 0 | 0 | 0 | 0 |
| Total %: | 100 | 100 | 100 | 100 | 100 | 100 |

Unilamellar liposomes were produced using the Liposo-Fast-Basic unit (AVESTIN, Inc., 2450 Don Reid Dr. Ottawa, ON, CANADA K1H 1E1). This unit produces unilamellar liposomes by the manual extrusion of a multilamellar liposome suspension through a polycarbonate membrane of defined pore size, using gas-tight, glass syringes. The sample is passed through the membrane by pushing the sample back and forth between two syringes. 50 nm unilamellar liposomes were generated by extrusion using 400 nm polycarbon filter (×20 movements through the membrane filter), and similarly with a 200 nm, 100 nm and 50 nm polycarbon filter until the desired size is achieved.

Liposomes were wrapped following the procedure described by Yagi et al., (supra). Briefly, a wraposome core was created using 100% DOTAP and reconstitution with liposome buffer (as described above). The liposome core was extruded to 50 nm as described above. The liposome core was mixed with siRNA in a mole ratio of 1:26 siRNA:lipid. The different types of siRNA used in the experiments are shown in Table 3. The wraposome was dissolved with 100% ethanol. Since lipids will not form liposomes in ethanol, but instead remain in solution, the amount of extra liposome buffer to be added was calculated to ensure that the final ethanol percentage is less than the maximum (i.e. the percentage of ethanol that will destabilize and dissolve the liposomal structures) to determine final volume required to attain the desired concentration of wraposomes. Liposomal buffer was added to the siRNA+core, followed by envelope solution with constant, but moderate, vortexing. Ethanol was then removed from the liposomes.

Example 13: Liposomes were Shown to Contain siRNA

Figure 21:
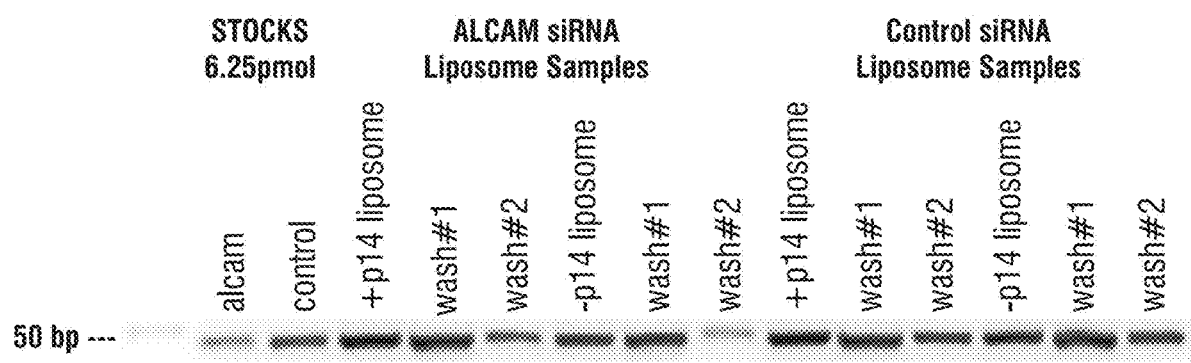
FIG. 21 represents siRNA electrophoresis for loading quantification.

Relative siRNA concentrations were detected using gel electrophoresis methods. Serial dilutions of siRNA were electrophoresed and the signal of each sample determined by estimating the ethidium bromide signal bound to the siRNA (see FIG. 21). A standard curve was then generated. Alternatively, a known amount of siRNA was loaded and used as a comparison to quantitate siRNA loading. The signal associated with the samples were then compared to the standard curve. The relative loading efficiencies are shown in Table 4.

TABLE 3

| Oligo Set # | Sense or Antisense | Oligo Name | 5'- Label | Sequence (5'--->3') |
|---|---|---|---|---|
| 1 | Sense | GFP_s | — | GGCUACGUCCAGGAG CGCACC (SEQ ID NO: 20) |
| 1 | Antisense | GFP_as | — | GCGCUCCUGGACGUA GCCUU (SEQ ID NO: 21) |
| 2 | Sense | ALCAM_s | — | AAGCCCGAUGGCUCC CCAGUAUU (SEQ ID NO: 22) |
| 2 | Antisense | ALCAM_as | — | AAUACUGGGGAGCCA UCGGGCUU (SEQ ID NO: 23) |
| 3 | Sense | SSB_s | — | ACAACAGACUUUAAU GUAAUU (SEQ ID NO: 24) |
| 3 | Antisense | SSB_as | — | UUACAUUAAAGUCUG UUGUUU (SEQ ID NO: 25) |
| 4 | Sense | Control_s | — | UCUUUUAACUCUCUU CAGGUU (SEQ ID NO: 26) |
| 4 | Antisense | Control_as | — | CCUGAAGAGAGUUAA AAGAU (SEQ ID NO: 27) |
| 5 | Sense | ALCAM_s | Cy5 | AAGCCCGAUGGCUCC CCAGUAUU (SEQ ID NO: 28) |
| 5 | Antisense | ALCAM_as | Cy5 | AAUACUGGGGAGCCA UCGGGCUU (SEQ ID NO: 29) |

TABLE 4

| Liposomes | siRNA | % Loading |
|---|---|---|
| +p14 | ALCAM | 34.5 |
| −p14 | ALCAM | 40 |
| +p14 | Control | 33.3 |
| −p14 | Control | 30.2 |

Example 14: Preparation of FAST Protein Containing Liposomes

For any liposomal preparation especially where a lipid profile is altered in any way, an optimal n-octyl β-D-glucopyranoside (OG) concentration for inserting FAST protein should be determined. The optimal concentration is just below the critical OG concentration which causes dissolution of the liposomes.

Insertion of the p14 FAST protein into the membrane of the liposome was accomplished generally by the detergent depletion method. Briefly, the purified FAST protein was reconstituted into liposomes by mixing detergent-suspended FAST protein with liposomes pre-saturated with detergent, followed by removal of the detergent.

Example 15: General Procedure for Studying siRNA Function

HT1080 cells were seeded on cover slips in 24 or 12 well cell culture plates and grown overnight. Seeding density was such that 50-60% confluence was achieved. The ability to see single cells is desired. Cells were gradually cooled to 4° C. by placing the plates in a standard refrigerator. Cells were washed gently with similarly cooled PBS. Liposomes with various cargoes were added to a final maximum of 1 mM lipid and incubated at 4° C. for 60 min. Cells were gently washed with cold PBS to then remove any unbound liposomes. Pre-warmed (37° C.) PBS was then added to initiate delivery of liposomal cargo. At the appropriate time, cells were rapidly cooled to 4° C. in ice water and then fixed (15 min in 1% formalin) and mounted with DAPI/Prolong Gold (Invitrogen). Slides were sealed to maintain the fluorescent signal for as long as possible. Fluorescent signal detection, imaging and quantitation was performed using an upright epifluorescent microscope with a motorized Z stage (Zeiss AxioImager.Z1 microscope, Carl Zeiss, Thornwood, N.Y., USA) controlled by Volocity (Version 5.4, Improvision, Lexington, Mass.). All exposures were kept constant across samples within the same experiment, and all contrasting for image presentation was similarly kept constant for all fluorescent channels. A minimum of 5 fields of view were analyzed and at least eighty individual cells are imaged and data quantitated per field of view. Graphing and statistics were performed using GraphPad Prism (version 4.00 for Windows, GraphPad Software, San Diego Calif., USA).

Example 16: Uptake of siRNA into Cancer Cells was Enhanced by FAST Protein Containing Liposomes Liposomes containing DOPC:DOPE:Cholesterol:DC-Cholesterol:PC-NBD:PC in a ratio of 58:30:4:6:1:1 were prepared as described above and siRNA introduced in a 1:26 siRNA:lipid mole ratio. P14 was added to the membrane of the liposome as described above.

Figure 22B:
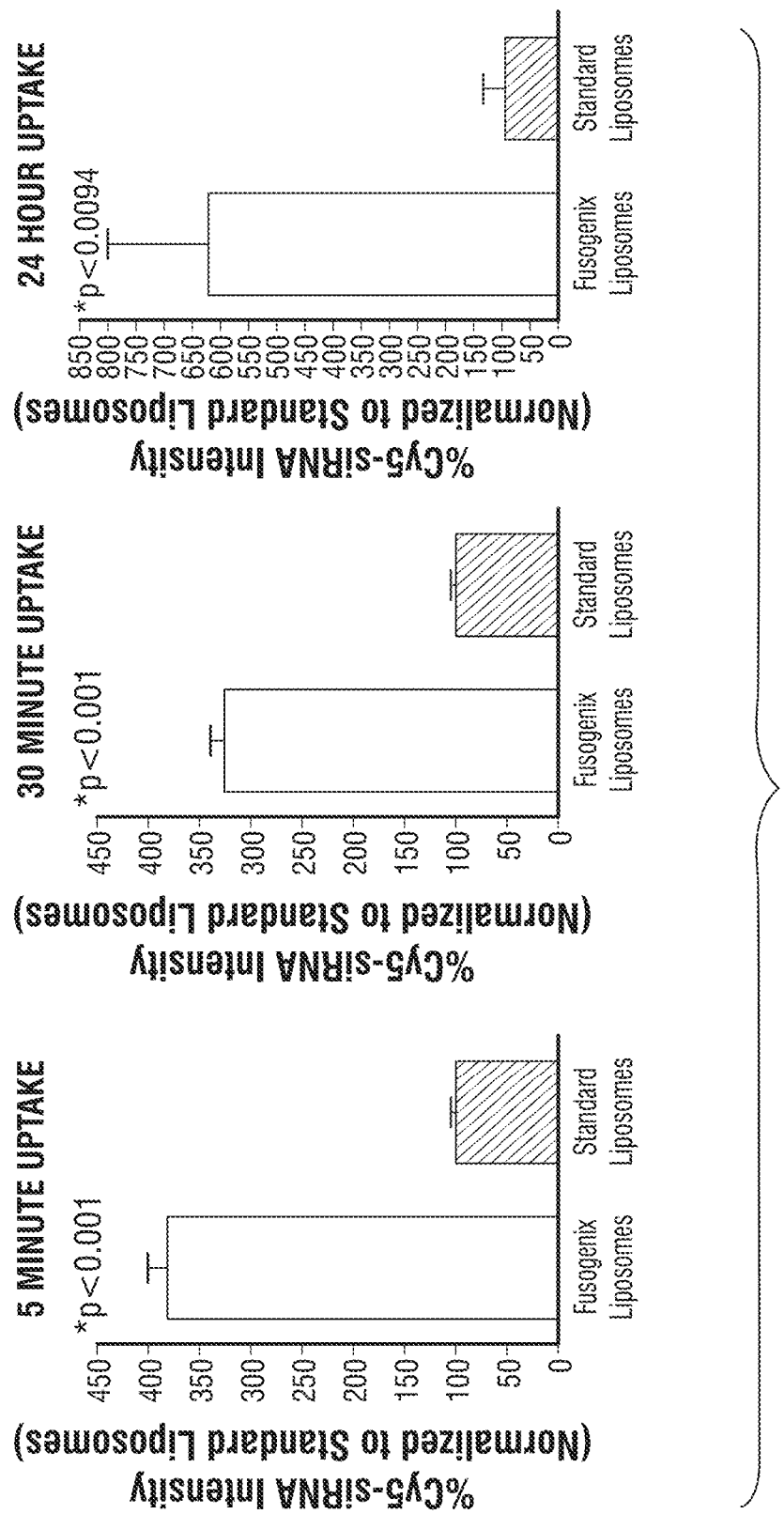

FIG. 22A shows that FAST protein containing liposomes are capable of delivering siRNA more rapidly to cells than standard liposomes, which did not contain the FAST protein in their membranes. Twenty-four hours after incubation, the FAST protein containing liposomes increased the amount of siRNA in the cells compared to standard liposomes (FIG. 22B).

Figure 23A:
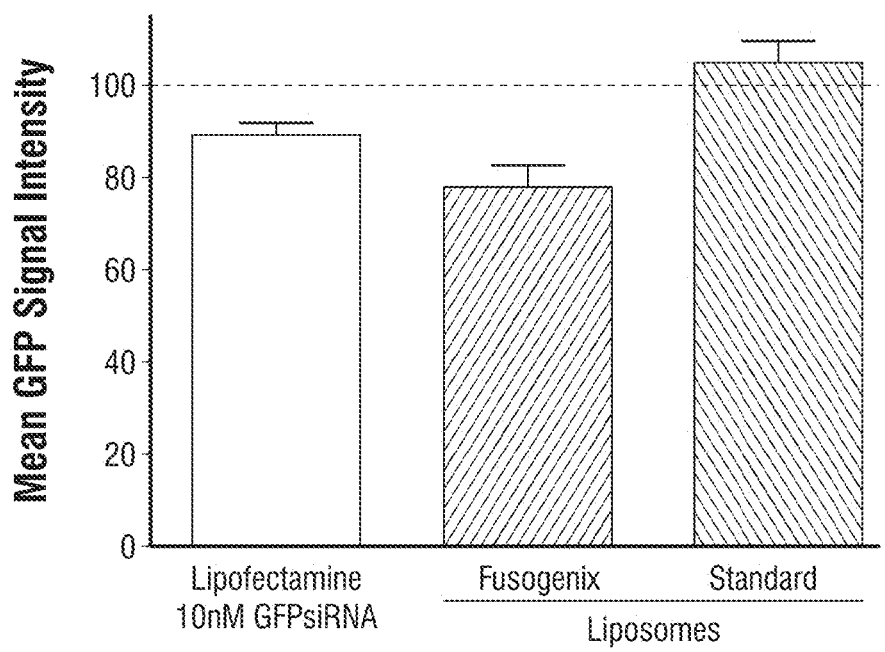
FIG. 23A is a graphical representation and FIG. 23B is an immunofluorescence image of GFP expression in HT1080 cells following delivery of siRNA using liposomes having fusogenic proteins embedded in their membrane compared to delivery by standard liposomes.
Figure 23B:
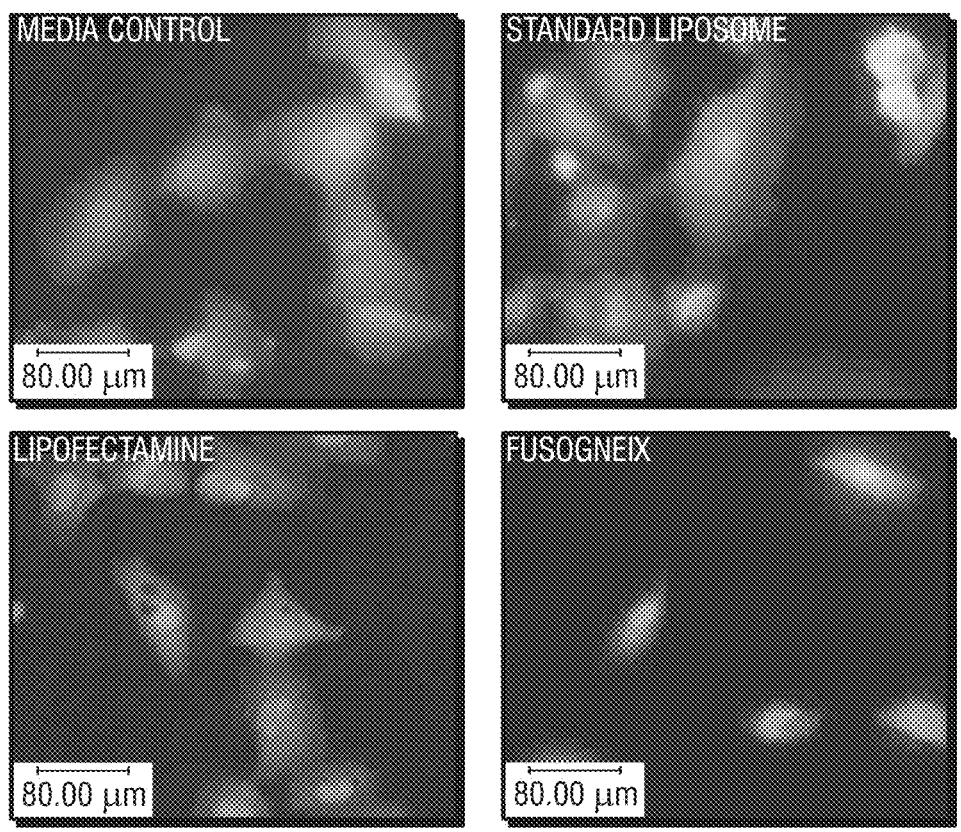

Example 17: FAST Protein Containing Liposomes Enhance siRNA-Mediated Knockdown of Functional Protein Compared to Standard Liposomes The expression of GFP in HT-1080 cells was assessed using fluorescent quantitation. Cells that had undergone no treatment were used as baseline estimation (100% expression). All other treatments were normalized to this expression level (relative signal intensity/cell). In these experiments, FAST protein containing liposomes were able to generate a significant reduction in GFP expression when compared to the media controls, and the standard liposomes (see FIG. 23A and FIG. 23B). No statistical significant difference was noted between the lipofectamine treatments and the FAST protein containing liposome treatments. However, the FAST protein containing liposomes were more effective in reducing GFP expression than lipofectamine treated cells.

What is claimed is:

1. A recombinant polypeptide for facilitating membrane fusion, said recombinant polypeptide comprising: an ectodomain sequence having the sequence of SEQ ID NO: 2 that comprises a functional myristoylation motif; a transmembrane domain comprising the sequence of SEQ ID NO: 11; and an endodomain sequence having the sequence of SEQ ID NO: 3.

2. The recombinant polypeptide of claim 1, wherein the polypeptide is operably linked to a targeting ligand.

3. The recombinant polypeptide of claim 2, wherein the targeting ligand is bombesin.

4. The recombinant polypeptide of claim 1, comprised within a liposome.

5. A recombinant polypeptide for facilitating membrane fusion, said recombinant polypeptide comprising: (a) an ectodomain sequence comprising a functional myristoylation motif; (b) a transmembrane domain comprising the sequence of SEQ ID NO: 11; and (c) an endodomain sequence; all operably linked to form a biologically-active fusion-associated small transmembrane (FAST) protein; wherein (i) the ectodomain sequence is obtained from a p10, a p14, and a p22 FAST protein and the endodomain sequence is obtained from a p10, a p14, a p15, and a p22 FAST protein or (ii) the ectodomain sequence is obtained from a p10, a p14, a p15, and a p22 FAST protein and the endodomain sequence is obtained from a p10, a p14, and a p22 FAST protein, wherein the ectodomain sequence comprises the sequence of SEQ ID NO: 2, and the endodomain sequence comprises the sequence of SEQ ID NO: 3 or SEQ ID NO: 4.

6. A biologically-active, hybrid or chimeric FAST protein comprising: (a) an ectodomain sequence that comprises a functional myristoylation motif; (b) a transmembrane domain having the sequence of SEQ ID NO: 11; and (c) an endodomain sequence; all of which are operably linked; and wherein the ectodomain sequence and the endodomain sequence are each obtained from one or more p10, p14, p15, and p22 FAST proteins, wherein the ectodomain sequence comprises the sequence of SEQ ID NO: 2, and the endodomain sequence comprises the sequence of SEQ ID NO: 3 or SEQ ID NO: 4.

7. A composition comprising:
(a) the recombinant polypeptide of claim 1 or claim 5; and
(b) a diluent, a liposome, a buffer, or any combination thereof.

8. A kit comprising, in a suitable container, (a) the recombinant polypeptide of claim 1 or claim 5, or the biologically-active, hybrid or chimeric FAST protein of claim 6; and (b) instructions for using the recombinant polypeptide or the biologically-active, hybrid or chimeric FAST protein in a method of inducing cell-cell fusion and heterokaryon formation in an animal cell.

* * * * *

```
                            SEQUENCE LISTING

<160> NUMBER OF SEQ ID NOS: 29

<210> SEQ ID NO 1
<211> LENGTH: 159
<212> TYPE: PRT
<213> ORGANISM: Artificial Sequence
<220> FEATURE:
<223> OTHER INFORMATION: Recombinant Polypeptide

<400> SEQUENCE: 1

Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Phe Val Glu Ile Val Ser Ser Thr Gly Ile Ile
        35                  40                  45

Ile Ala Val Gly Ile Phe Ala Phe Ile Phe Ser Phe Leu Tyr Lys Leu
    50                  55                  60

Leu Gln Trp Tyr Asn Arg Lys Ser Lys Asn Lys Lys Arg Lys Glu Gln
65                  70                  75                  80

Ile Arg Glu Gln Ile Glu Leu Gly Leu Leu Ser Tyr Gly Ala Gly Val
                85                  90                  95

Ala Ser Leu Pro Leu Leu Asn Val Ile Ala His Asn Pro Gly Ser Val
            100                 105                 110

Ile Ser Ala Thr Pro Ile Tyr Lys Gly Pro Cys Thr Gly Val Pro Asn
        115                 120                 125

Ser Arg Leu Leu Gln Ile Thr Ser Gly Thr Ala Glu Glu Asn Thr Arg
    130                 135                 140

Ile Leu Asn His Asp Gly Arg Asn Pro Asp Gly Ser Ile Asn Val
145                 150                 155

<210> SEQ ID NO 2
<211> LENGTH: 38
<212> TYPE: PRT
<213> ORGANISM: Reovirus

<400> SEQUENCE

Gly Val Ala Ser Leu Pro Leu Leu Asn Val Ile Ala His Asn Pro Gly
            35                  40                  45

Ser

<210> SEQ ID NO 4
<211> LENGTH: 48
<212> TYPE: PRT
<213> ORGANISM: REOVIRUS

<400> SEQUENCE: 4

Val Ile Ser Ala Thr Pro Ile Tyr Lys Gly Pro Cys Thr Gly Val Pro
1               5                   10                  15

Asn Ser Arg Leu Leu Gln Ile Thr Ser Gly Thr Ala Glu Glu Asn Thr
            20                  25                  30

Arg Ile Leu Asn His Asp Gly Arg Asn Pro Asp Gly Ser Ile Asn Val
            35                  40                  45

<210> SEQ ID NO 5
<211> LENGTH: 477
<212> TYPE: DNA
<213> ORGANISM: Artificial Sequence
<220> FEATURE:
<223> OTHER INFORMATION: Recombinant polypeptide coding sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t -continued

```
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
```

```
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
```

```
-continued

<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
```

```
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
```

```
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<400> SEQUENCE: 5
atgggnwsng gnccnwsnaa yttygtnaay caygcnccng gngargcnat hgtnacnggn 60
ytngaraarg gngcngayaa rgtngcnggn acnathwsnc ayacnathtt ygtngarath 120
gtnwsnwsnw snacnggnat hathathgcn gtnggnatht tygcnttyat httywsntty 180
ytntayaary tnytncartg gtayaaymgn aarwsnaara ayaaraarmg naargarcar 240
athmgngarc arathgaryt nggnytnytn wsntayggng cnggngtngc nwsnytnccn 300
ytnytnaayg tnathgcnca yaayccnggn wsngtnathw sngcnacncc nathtayaar 360
ggnccntgya cnggngtncc naaywsnmgn ytnytncara thacnwsngg nacngcngar 420
garaayacnm gnathytnaa ycaygayggn mgnaayccng ayggnwsnat haaygtn 477

<210> SEQ ID NO 6
<211> LENGTH: 114
<212> TYPE: DNA
<213> ORGANISM: REOVIRUS

<400> SEQUENCE: 6
atggggagtg gaccctctaa tttcgtcaat cacgcacctg gagaagcaat tgtaaccggt 60
ttggagaaag ggcagataa agtagctgga acgatatcac atacgatttg ggaa 114

<210> SEQ ID NO 7
<211> LENGTH: 294
<212> TYPE: DNA
<213> ORGANISM: REOVIRUS

<400> SEQUENCE: 7
aagttgctgc agtggtacaa tcgtaagtca aagaataaga aacgtaaaga gcaaattaga 60
gaacaaattg agcttggttt attatcatat ggtgctggag tagcatcact tcctttgctc 120
aacgttattg cacataatcc tggatcagtt atctcggcta cccctatcta taaaggtccg 180
tgcactggtg tacctaattc gcgcctactt caaatcacga gcgggactgc agaagagaac 240
actagaattt tgaatcatga tggaagaaac ccagatggaa gtatcaacgt ttga 294

<210> SEQ ID NO 8
<211> LENGTH: 20
<212> TYPE: PRT
<213> ORGANISM: Reovirus

<400> SEQUENCE: 8

Leu Gly Leu Leu Ser Tyr Gly Ala Gly Val Ala Ser Leu Pro Leu Leu
1 5 10 15

Asn Val Ile Ala
20

<210> SEQ ID NO 9
<211> LENGTH: 20
<212> TYPE: PRT
<213> ORGANISM: Reovirus

```
<400> SEQUENCE: 9

Val Leu Ala Pro Gly Leu Asn Ala Leu Ser Leu Gly Val Leu Ala Ser
1               5                   10                  15

Leu Ile Tyr Gly
            20

<210> SEQ ID NO 10
<211> LENGTH: 30
<212> TYPE: PRT
<213> ORGANISM: Reovirus

<400> SEQUENCE: 10

Gly Ser Gly Pro Ser Asn Phe Val Asn His Ala Pro Gly Glu Ala Ile
1               5                   10                  15

Val Thr Gly Leu Glu Lys Gly Ala Asp Lys Val Ala Gly Thr
            20                  25                  30

<210> SEQ ID NO 11
<211> LENGTH: 23
<212> TYPE: PRT
<213> ORGANISM: Artificial Sequence
<220> FEATURE:
<223> OTHER INFORMATION: Recombinant Polypeptide

<400> SEQUENCE: 11

Ile Val Ser Ser Ser Thr Gly Ile Ile Ile Ala Val Gly Ile Phe Ala
1               5                   10                  15

Phe Ile Phe Ser Phe Leu Tyr
            20

<210> SEQ ID NO 12
<211> LENGTH: 22
<212> TYPE: PRT
<213> ORGANISM: Artificial Sequence
<220> FEATURE:
<223> OTHER INFORMATION: Recombinant Polypeptide

<400> SEQUENCE: 12

Val Ser Ser Ser Thr Gly Ile Ile Ile Ala Val Gly Ile Phe Ala Phe
1               5                   10                  15

Ile Phe Ser Phe Leu Tyr
            20

<210> SEQ ID NO 13
<211> LENGTH: 21
<212> TYPE: PRT
<213> ORGANISM: Artificial Sequence
<220> FEATURE:
<223> OTHER INFORMATION: Recombinant Polypeptide

<400> SEQUENCE: 13

Ser Ser Ser Thr Gly Ile Ile Ile Ala Val Gly Ile Phe Ala Phe Ile
1               5                   10                  15

Phe Ser Phe Leu Tyr
            20

<210> SEQ ID NO 14
<211> LENGTH: 19
<212> TYPE: PRT
<213> ORGANISM: Artificial Sequence
<220> FEATURE:
<223> OTHER INFORMATION: Recombinant Polypeptide
```

```
<400> SEQUENCE: 14

Ile Val Ser Ser Thr Gly Ile Ile Ile Ala Val Gly Ile Phe Ala
1               5                   10                  15

Phe Ile Phe

<210> SEQ ID NO 15
<211> LENGTH: 23
<212> TYPE: PRT
<213> ORGANISM: Artificial Sequence
<220> FEATURE:
<223> OTHER INFORMATION: Recombinant Polypeptide

<400> SEQUENCE: 15

Ala Val Ser Ser Thr Gly Ile Ile Ile Ala Val Gly Ile Phe Ala
1               5                   10                  15

Phe Ile Phe Ser Phe Leu Tyr
            20

<210> SEQ ID NO 16
<211> LENGTH: 23
<212> TYPE: PRT
<213> ORGANISM: Artificial Sequence
<220> FEATURE:
<223> OTHER INFORMATION: Recombinant Polypeptide

<400> SEQUENCE: 16

Ala Ala Ser Ser Thr Gly Ile Ile Ile Ala Val Gly Ile Phe Ala
1               5                   10                  15

Phe Ile Phe Ser Phe Leu Tyr
            20

<210> SEQ ID NO 17
<211> LENGTH: 150
<212> TYPE: PRT
<213> ORGANISM: Artificial Sequence
<220> FEATURE:
<223> OTHER INFORMATION: Recombinant Polypeptide

<400> SEQUENCE: 17

Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Trp Glu Val Ile Ala Gly Leu Val Ala Leu Leu Thr
        35                  40                  45

Phe Leu Ala Phe Gly Phe Trp Leu Phe Lys Tyr Leu Gln Lys Arg Arg
    50                  55                  60

Glu Arg Arg Arg Gln Leu Thr Glu Phe Gln Lys Arg Tyr Leu Arg Asn
65                  70                  75                  80

Ser Tyr Arg Leu Ser Glu Ile Gln Arg Pro Ile Ser Gln His Glu Tyr
                85                  90                  95

Glu Asp Pro Tyr Glu Pro Pro Ser Arg Arg Lys Pro Pro Pro Pro Pro
            100                 105                 110

Tyr Ser Thr Tyr Val Asn Ile Asp Asn Val Ser Ala Ile Asp Asp Asp
        115                 120                 125

Asp Lys His His His His His His Glu Gln Arg Leu Gly Asn Gln Trp
    130                 135                 140

Ala Val Gly His Leu Met
145                 150
```

```
<210> SEQ ID NO 18
<211> LENGTH: 453
<212> TYPE: DNA
<213> ORGANISM: Artificial Sequence
<220> FEATURE:
<223> OTHER INFORMATION: Polypeptide coding sequence

<400> SEQUENCE: 18
atggggagtg gaccctctaa tttcgtcaat cacgcacctg agaagcaatt tgtaaccggt      60
ttggagaaag gggcagataa agtagctgga acgatatcac atacgatttg ggaagtgatc     120
gccggattag tagccttgct gacattctta gcgtttggct tctggttgtt caagtatctc     180
caaaagagaa gagaaagaag gagacaactc actgagttcc aaaaacggta tctacggaat     240
agctacaggt tgagtgagat ccagagacct atatcacagc acgaatacga agacccatac     300
gagccaccaa gtcgtaggaa accacccccct cctccttata gcacatacgt caacatcgat     360
aatgtctcag ccattgatga cgacgacaag caccatcacc accatcacga gcagaggctg     420
gggaatcagt gggcagtggg tcacttgatg taa                                 453

<210> SEQ ID NO 19
<211> LENGTH: 8
<212> TYPE: PRT
<213> ORGANISM: Reovirus

<400> SEQUENCE: 19

Gly Ser Gly Pro Ser Asn Phe Val
1               5

<210> SEQ ID NO 20
<211> LENGTH: 21
<212> TYPE: RNA
<213> ORGANISM: Artificial Sequence
<220> FEATURE:
<223> OTHER INFORMATION: siRNA Oligo GFP_s

<400> SEQUENCE: 20
ggcuacgucc aggagcgcac c                                               21

<210> SEQ ID NO 21
<211> LENGTH: 20
<212> TYPE: RNA
<213> ORGANISM: Artificial Sequence
<220> FEATURE:
<223> OTHER INFORMATION: siRNA Oligo GFP_as

<400> SEQUENCE: 21
gcgcuccugg acguagccuu                                                 20

<210> SEQ ID NO 22
<211> LENGTH: 23
<212> TYPE: RNA
<213> ORGANISM: Artificial Sequence
<220> FEATURE:
<223> OTHER INFORMATION: siRNA Oligo ALCAM_s

<400> SEQUENCE: 22
aagcccgaug gcuccccagu auu                                             23

<210> SEQ ID NO 23
<211> LENGTH: 23
<212> TYPE: RNA
<213> ORGANISM: Artificial Sequence
<220> FEATURE:
<223> OTHER INFORMATION: siRNA Oligo ALCAM_as
```

```
<400> SEQUENCE: 23
aauacugggg agccaucggg cuu                                              23

<210> SEQ ID NO 24
<211> LENGTH: 19
<212> TYPE: RNA
<213> ORGANISM: Artificial Sequence
<220> FEATURE:
<223> OTHER INFORMATION: siRNA Oligo SSB_s

<400> SEQUENCE: 24
acaacagacu uuaauguaa                                                   19

<210> SEQ ID NO 25
<211> LENGTH: 21
<212> TYPE: RNA
<213> ORGANISM: Artificial Sequence
<220> FEATURE:
<223> OTHER INFORMATION: siRNA Oligo SSB_as

<400> SEQUENCE: 25
uuacauuaaa gucuguuguu u                                                21

<210> SEQ ID NO 26
<211> LENGTH: 19
<212> TYPE: RNA
<213> ORGANISM: Artificial Sequence
<220> FEATURE:
<223> OTHER INFORMATION: siRNA Oligo Control_s

<400> SEQUENCE: 26
ucuuuuaacu cucuucagg                                                   19

<210> SEQ ID NO 27
<211> LENGTH: 20
<212> TYPE: RNA
<213> ORGANISM: Artificial Sequence
<220> FEATURE:
<223> OTHER INFORMATION: siRNA Oligo Control_as

<400> SEQUENCE: 27
ccugaagaga guuaaaagau                                                  20

<210> SEQ ID NO 28
<211> LENGTH: 23
<212> TYPE: RNA
<213> ORGANISM: Artificial Sequence
<220> FEATURE:
<223> OTHER INFORMATION: siRNA Oligo ALCAM_s

<400> SEQUENCE: 28
aagcccgaug gcuccccagu auu                                              23

<210> SEQ ID NO 29
<211> LENGTH: 23
<212> TYPE: RNA
<213> ORGANISM: Artificial Sequence
<220> FEATURE:
<223> OTHER INFORMATION: siRNA Oligo ALCAM_as

<400> SEQUENCE: 29
aauacugggg agccaucggg cuu                                              23
```